United States Patent
Khlat et al.

(10) Patent No.: US 8,159,309 B1
(45) Date of Patent: Apr. 17, 2012

(54) WINDOWING TO NARROW A BANDWIDTH OF AN AMPLITUDE MODULATION POWER SUPPLY INPUT SIGNAL

(75) Inventors: Nadim Khlat, Cugnaux (FR); David Reed, Colorado Springs, CO (US)

(73) Assignee: RF Micro Devices, Inc., Greensboro, NC (US)

( * ) Notice: Subject to any disclaimer, the term of this patent is extended or adjusted under 35 U.S.C. 154(b) by 117 days.

(21) Appl. No.: 12/822,848

(22) Filed: Jun. 24, 2010

Related U.S. Application Data

(60) Provisional application No. 61/219,996, filed on Jun. 24, 2009.

(51) Int. Cl.
 H03C 1/02 (2006.01)
 H03C 1/06 (2006.01)
 H03C 3/02 (2006.01)
 H03C 3/08 (2006.01)

(52) U.S. Cl. ........ 332/159; 332/103; 332/145; 332/151; 332/160

(58) Field of Classification Search .......... 332/103–105, 332/144, 145, 149, 151–154, 159, 160
See application file for complete search history.

(56) References Cited

U.S. PATENT DOCUMENTS 8,064,852 B2 * 11/2011 Pennec ................... 455/126

* cited by examiner

Primary Examiner — David Mis
(74) Attorney, Agent, or Firm — Withrow & Terranova, P.L.L.C.

(57) ABSTRACT

The present disclosure relates to using windowing to reduce the bandwidth of an amplitude modulation (AM) power supply input signal (PSIS), which is fed to an AM power supply to provide envelope power to an RF power amplifier stage via an AM power supply output signal. By reducing the bandwidth, noise levels from the AM power supply may be reduced. However, although the bandwidth of the AM PSIS is reduced, the AM power supply output signal may track the AM of the RF power amplifier stage closely enough to meet linearity requirements and to provide high efficiency. The windowing may be based on dividing a stream of AM input samples into a stream of input windows, from which a stream of output windows is created to provide a stream of windowed AM input samples that are used to provide a windowed AM PSIS to the AM power supply.

27 Claims, 22 Drawing Sheets

WINDOWING TO NARROW A BANDWIDTH OF AN AMPLITUDE MODULATION POWER SUPPLY INPUT SIGNAL

This application claims the benefit of provisional patent application Ser. No. 61/219,996, filed Jun. 24, 2009, the disclosure of which is hereby incorporated herein by reference in its entirety.

FIELD OF THE DISCLOSURE

Embodiments of the present invention relate to amplitude-modulated radio frequency (RF) power amplifiers, including polar-modulated RF power amplifiers that are powered using amplitude-modulated power supplies, which may be used in RF communications systems.

BACKGROUND OF THE DISCLOSURE

As technology progresses, portable devices tend to integrate more features. For example, portable devices may include features associated with personal digital assistants (PDAs), cellular telephones, wireless internet access devices, global positioning system (GPS) receivers, and the like. Such portable devices may support one or more wireless communications protocols, such as third (3G), fourth (4G), or later generation cellular telephone protocols, GPS protocols, wireless fidelity (Wi-Fi) protocols, Bluetooth®, and the like. Some of these protocols may have tight channel spacing that require narrow channel bandwidths and tight restrictions on transmissions of spurious RF signals outside a channel's bandwidth. Often, to meet channel bandwidth requirements and to meet spurious RF emissions requirements, an RF transmitter may need to meet stringent linearity and noise requirements. An RF power amplifier in an RF transmitter may be a major source of non-linearity; therefore, there is a need for an RF power amplifier that meets stringent linearity requirements.

Most portable devices are battery powered and, since battery life is inversely related to power consumption, need to consume as little power as possible to maximize battery life. The RF power amplifier in a wireless portable device may consume a significant portion of the power used by the portable device. One way to reduce power consumption in an RF power amplifier is to improve its efficiency. Some communications protocols, such as those using wideband code division multiple access (WCDMA), may require polar modulation of an RF signal. Polar modulation includes an amplitude modulation (AM) component and a phase modulation (PM) component. To maximize efficiency in an amplitude-modulated or polar-modulated RF power amplifier, an envelope power supply input to the RF power amplifier may be provided by an AM power supply, which may include a switching power supply that tracks, at least to some extent, the amplitude of an amplitude-modulated or polar-modulated RF signal to the RF power amplifier.

Linearity of the RF power amplifier may be degraded when using a constant power supply due to modulation of the gain of the RF power amplifier by the RF envelope, which is associated with AM. Additionally, the AM power supply must provide adequate headroom for proper operation of the RF power amplifier. In some systems, such as 4G or later communications protocols, the bandwidth of an AM signal used to modulate the AM power supply may be about 12 megahertz or more; therefore, for proper tracking, the bandwidth of the AM power supply may need to be about 12 megahertz or more. Such an AM power supply may include a switching power supply and a linear power supply to meet bandwidth requirements; however, linear power supplies are typically less efficient than switching power supplies. Therefore, a 12 megahertz AM power supply may be less efficient than an AM power supply with less bandwidth. Further, a 12 megahertz AM power supply may push the boundaries of power supply technology, thereby introducing unacceptable levels of noise into the RF power amplifier. Thus, there is a need for RF power amplifier circuitry that includes an amplitude-modulated or polar-modulated RF power amplifier, which is powered from an AM power supply, maximizes efficiency, meets noise requirements, and meets linearity requirements.

SUMMARY OF THE EMBODIMENTS

The present disclosure relates to using windowing to reduce the bandwidth of an amplitude modulation (AM) power supply input signal (PSIS), which is fed to an AM power supply to provide envelope power to an RF power amplifier stage via an AM power supply output signal. By reducing the bandwidth, noise levels from the AM power supply may be reduced. However, although the bandwidth of the AM PSIS is reduced, the AM power supply output signal may track the AM of the RF power amplifier stage closely enough to meet linearity requirements and to provide high efficiency. The windowing may be based on dividing a stream of AM input samples into a stream of input windows, from which a stream of output windows is created to provide a stream of windowed AM input samples that are used to provide a windowed AM PSIS to the AM power supply. The number of samples in each input window is equal to the number of samples in each output window, and all of the samples in each output window have the same value, which is based on the samples in a corresponding input window.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION OF THE DISCLOSURE

The embodiments set forth below represent the necessary information to enable those skilled in the art to practice the disclosure and illustrate the best mode of practicing the disclosure. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The present disclosure relates to using windowing to reduce the bandwidth of an amplitude modulation (AM) power supply input signal (PSIS), which is fed to an AM power supply to provide envelope power to an RF power amplifier stage via an AM power supply output signal. By reducing the bandwidth, noise levels from the AM power supply may be reduced. However, although the bandwidth of the AM PSIS is reduced, the AM power supply output signal may track the AM of the RF power amplifier stage closely enough to meet linearity requirements and to provide high efficiency. The windowing may be based on dividing a stream of AM input samples into a stream of input windows, from which a stream of output windows is created to provide a stream of windowed AM input samples that are used to provide a windowed AM PSIS to the AM power supply. The number of samples in each input window is equal to the number of samples in each output window, and all of the samples in each output window have the same value, which is based on the samples in a corresponding input window.

Figure 1:
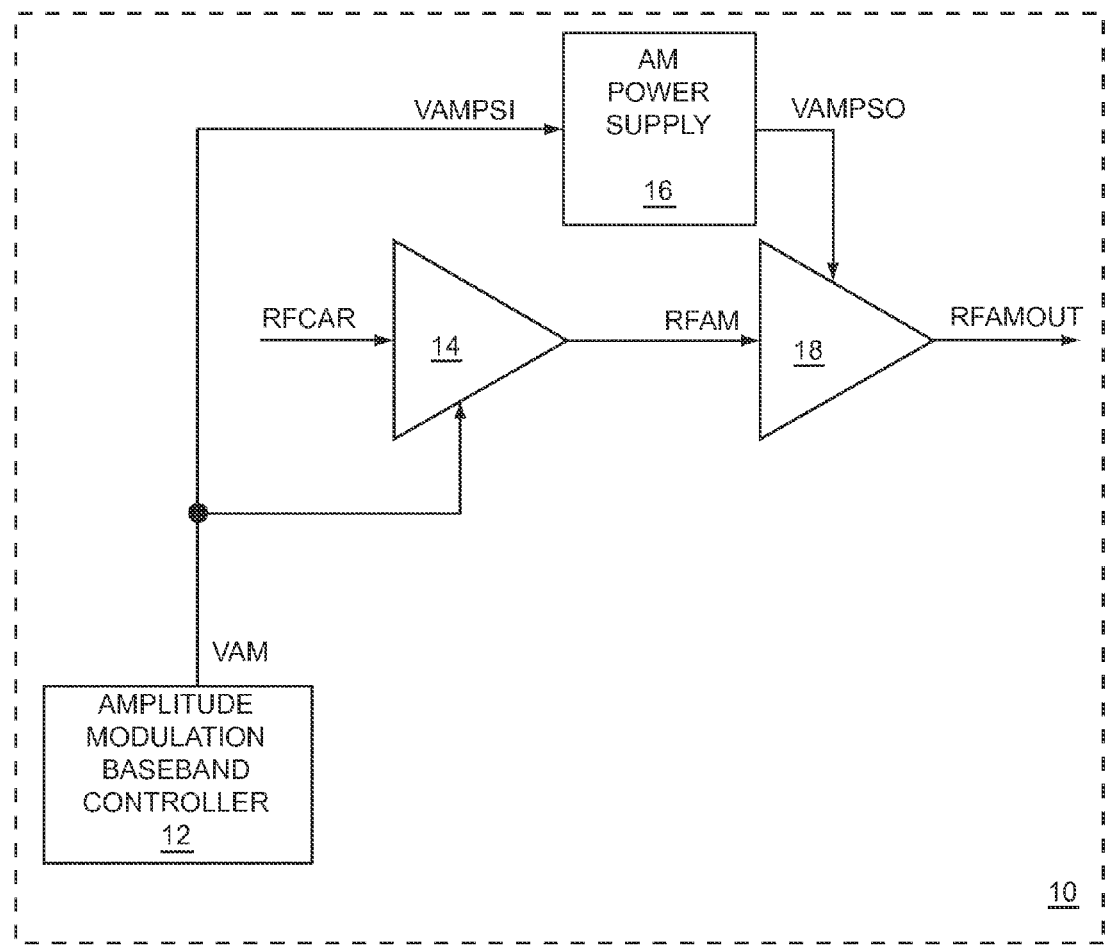
FIG. 1 shows an amplitude-modulated RF power amplifier circuit, according to the prior art.

FIG. 1 shows an amplitude-modulated RF power amplifier (PA) circuit 10, according to the prior art. AM is a modulation technique such that the amplitude of an RF carrier is modulated, which may be used to encode some kind of information. An AM baseband controller 12 provides an AM signal VAM to an AM modulation circuit 14. The AM signal VAM may provide an AM power supply input signal VAMPSI to an AM power supply 16, which provides an AM power supply output signal VAMPSO based on the AM power supply input signal VAMPSI. The AM modulation circuit 14 receives and amplitude-modulates an RF carrier signal RFCAR using the AM signal VAM to provide an AM RF input signal RFAM to a PA stage 18, which amplifies the AM RF input signal RFAM to provide an AM RF output signal RFAMOUT. The AM power supply output signal VAMPSO may provide power for amplification to the PA stage 18.

Figure 2:
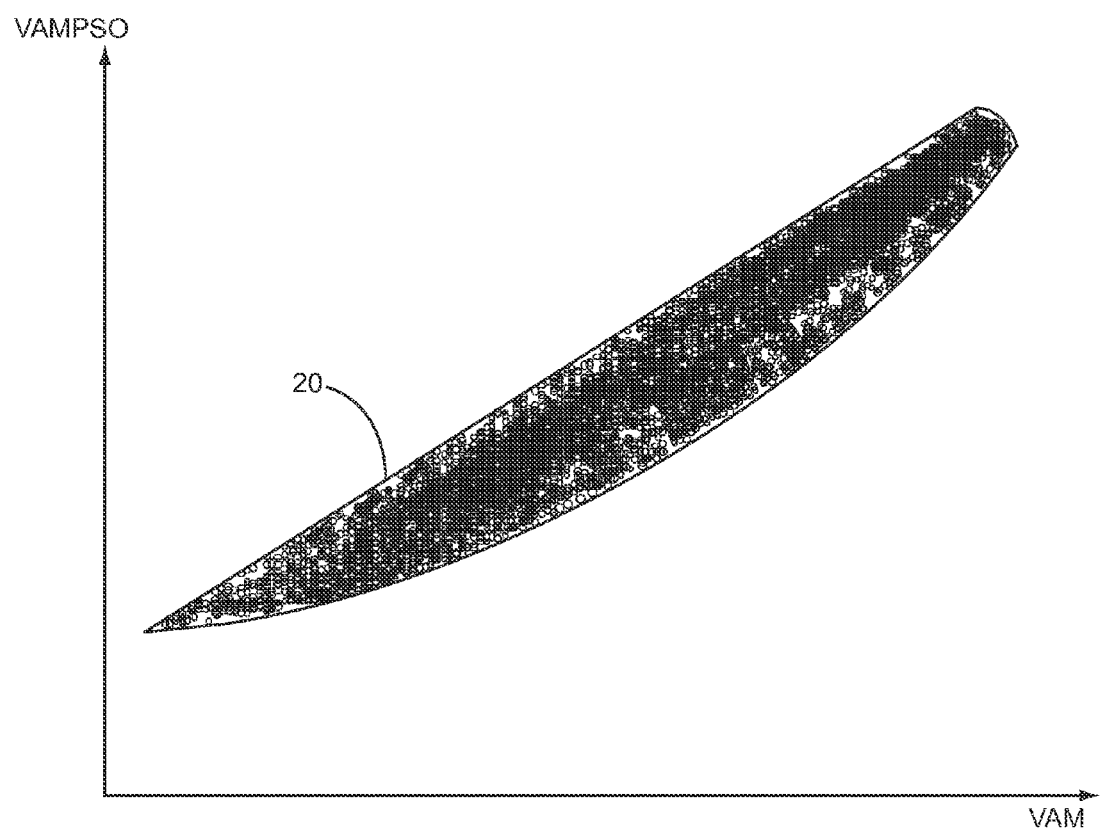
FIG. 2 is a graph showing simulation results of an amplitude modulation (AM) power supply output signal needed to maintain linearity versus an AM signal when a filtering bandwidth provided by an AM power supply in the amplitude-modulated RF power amplifier circuit is equal to seven megahertz, according to one example of the amplitude-modulated RF power amplifier circuit illustrated in FIG. 1.

FIG. 2 is a graph showing simulation results of the AM power supply output signal VAMPSO needed to maintain linearity versus the AM signal VAM when a filtering bandwidth provided by the AM power supply 16 is equal to seven megahertz, according to an example using a wideband code division multiple access (WCDMA) high-speed uplink packet access (HSUPA) greater than a category 3 (GTC3) test signal. Since the filtering behavior of the AM power supply 16 includes group delay, delay dispersion is introduced into the simulation. As a result, the graph illustrated in FIG. 2 may be represented as a first distribution 20, as shown.

Figure 3:
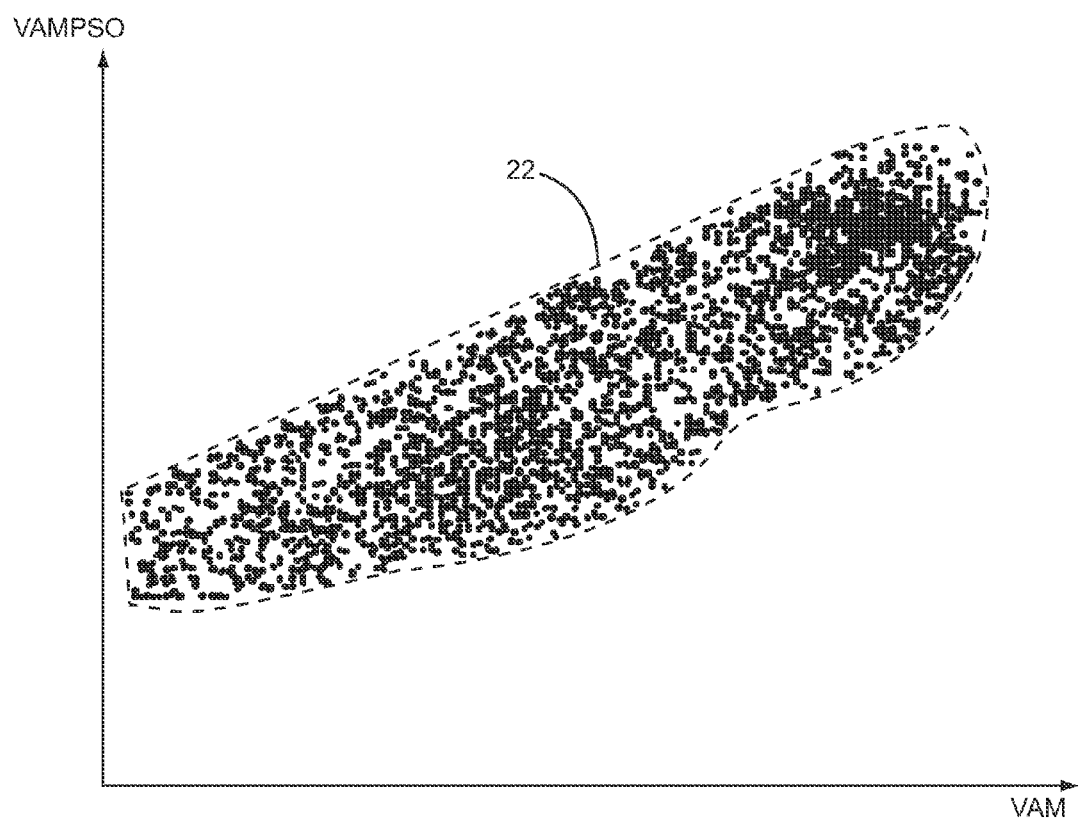
FIG. 3 is a graph showing simulation results of the AM power supply output signal versus the AM signal when the filtering bandwidth provided by the AM power supply is equal to two megahertz, according to another example of the amplitude-modulated RF power amplifier circuit illustrated in FIG. 1.

FIG. 3 is a graph showing simulation results of the AM power supply output signal VAMPSO versus the AM signal VAM when the filtering bandwidth provided by the AM power supply 16 is equal to two megahertz, according to the example using the WCDMA HSUPA GTC3 test signal. As a result, the graph illustrated in FIG. 3 may be represented as a second distribution 22, as shown.

Figure 4:
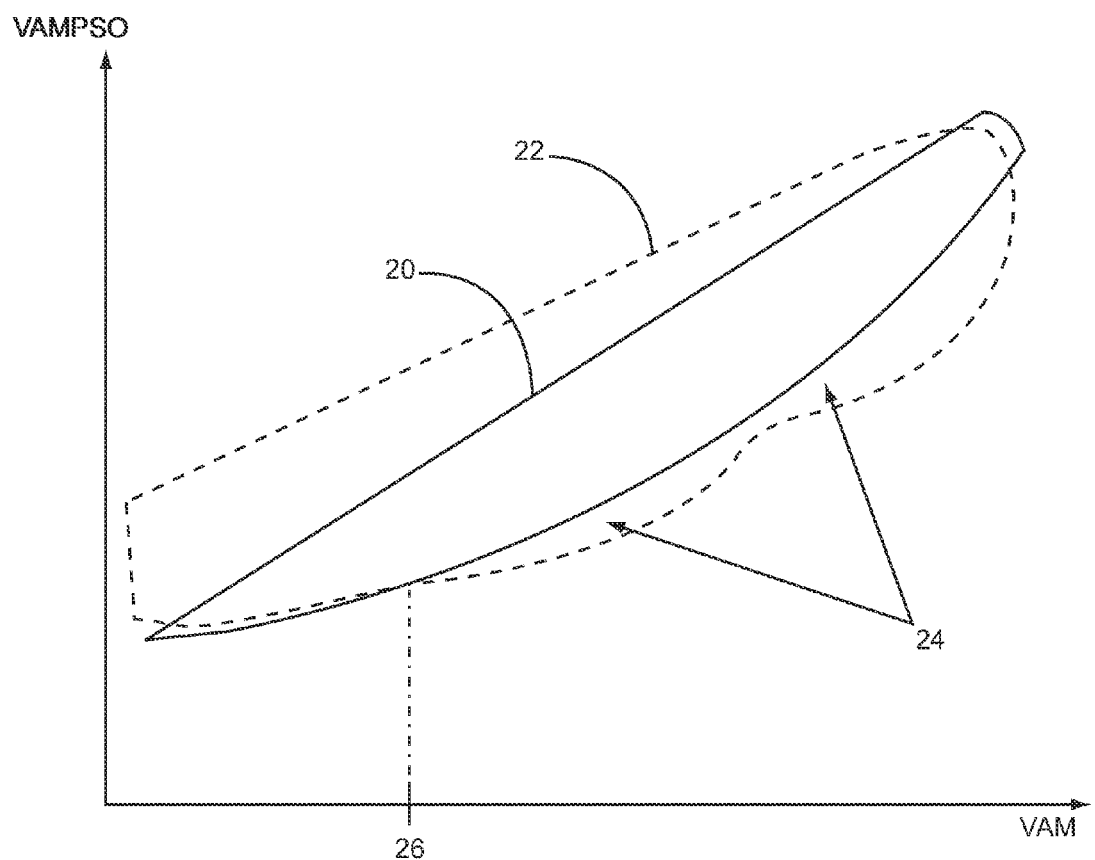
FIG. 4 is an overlay of a first distribution and a second distribution from FIGS. 2 and 3.

FIG. 4 is an overlay of the first distribution 20 and the second distribution 22 from FIGS. 2 and 3. Deficiency zones 24 occur when the second distribution 22 shows insufficient magnitude in the AM power supply output signal VAMPSO to maintain linearity. Therefore, operating the AM power supply 16 when its filtering bandwidth is equal to two megahertz may violate linearity requirements. However, when a magnitude of the AM signal VAM is less than a first threshold 26, the AM power supply 16, when its filtering bandwidth is equal to two megahertz, meets linearity requirements.

Figure 5:
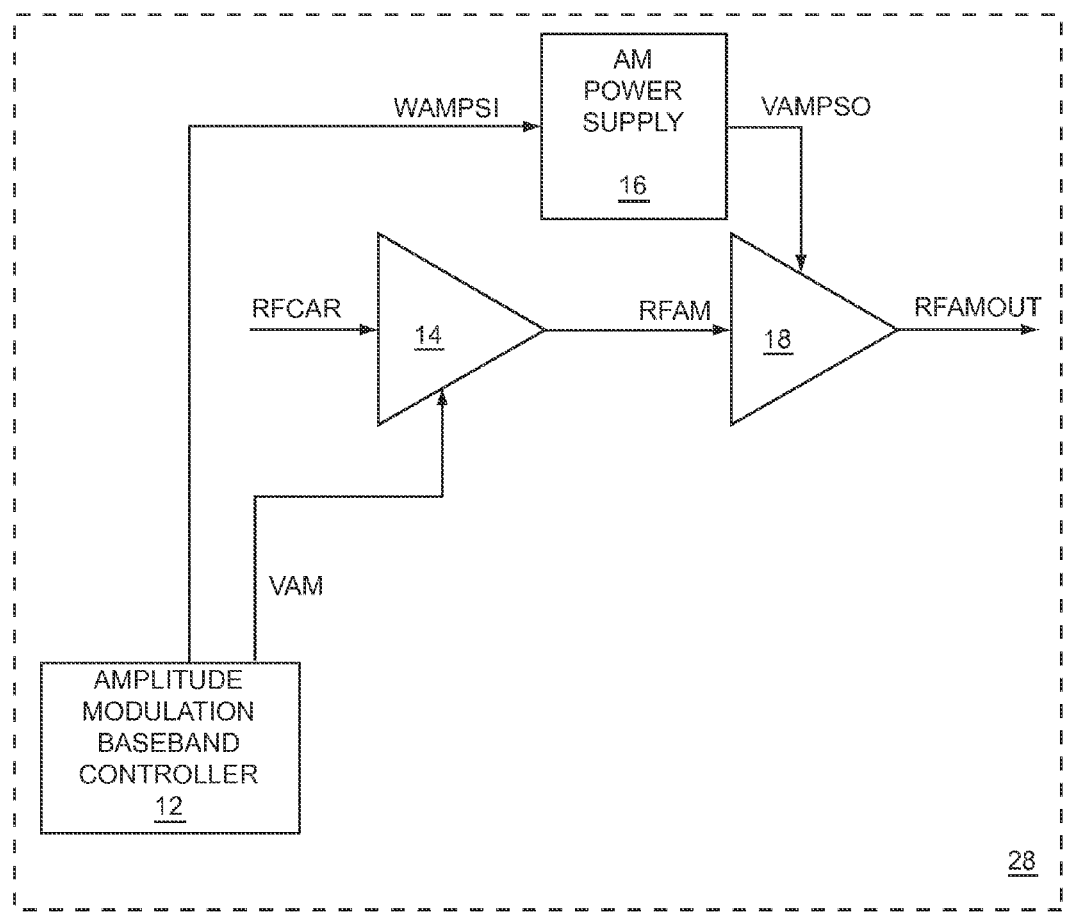
FIG. 5 shows a windowed amplitude-modulated RF power amplifier circuit, according to one embodiment of the present disclosure.

FIG. 5 shows a windowed amplitude-modulated RF PA circuit 28, according to one embodiment of the windowed amplitude-modulated RF PA circuit 28. The AM baseband controller 12 provides the AM signal VAM to the AM modulation circuit 14. Further, the AM baseband controller 12 provides a windowed AM power supply input signal WAMPSI to the AM power supply 16, which provides the AM power supply output signal VAMPSO based on the windowed AM power supply input signal WAMPSI. The AM modulation circuit 14 receives and amplitude-modulates the RF carrier signal RFCAR using the AM signal VAM to provide the AM RF input signal RFAM to the PA stage 18, which amplifies the AM RF input signal RFAM to provide the AM RF output signal RFAMOUT. The AM power supply output signal VAMPSO may provide power for amplification to the PA stage 18. Alternate embodiments of the windowed amplitude-modulated RF PA circuit 28 may include at least one additional PA stage coupled in series with the PA stage 18.

Figure 6:
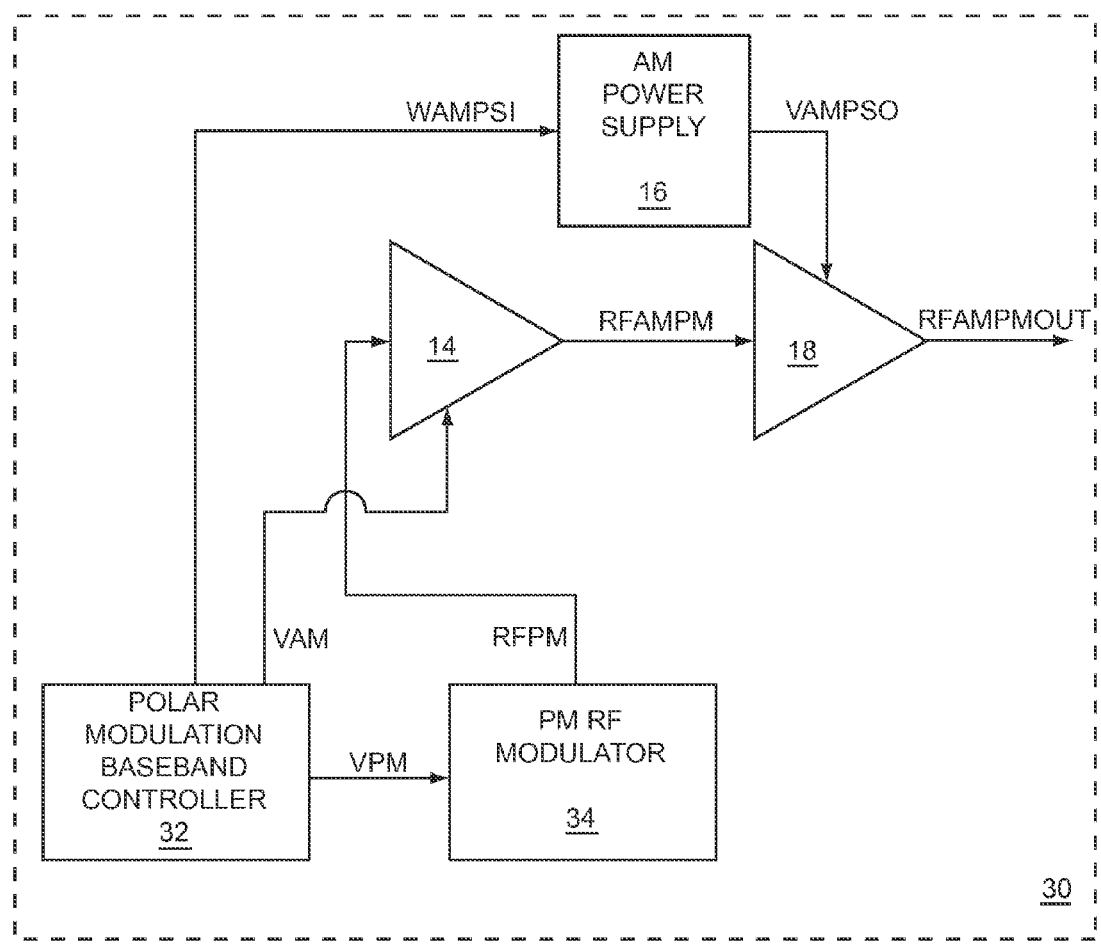
FIG. 6 shows a windowed polar-modulated RF power amplifier circuit, according to an alternate embodiment of the present disclosure.

FIG. 6 shows a polar-modulated RF power amplifier circuit 30, according to one embodiment of the polar-modulated RF power amplifier circuit 30. Phase modulation (PM) is a modulation technique such that the phase of an RF carrier is modulated, which may be used to encode some kind of information. PM may be combined with AM to provide polar modulation, which may provide encoding of more information than either PM or AM alone. A polar modulation baseband controller 32 provides the AM signal VAM to the AM modulation circuit 14 and a PM signal VPM to a PM RF modulator 34, which phase-modulates an RF carrier signal (not shown) using the PM signal VPM to provide a PM RF signal RFPM to the AM modulation circuit 14. The AM signal VAM may provide the windowed AM power supply input signal WAMPSI to the AM power supply 16, which provides the AM power supply output signal VAMPSO based on the windowed AM power supply input signal WAMPSI. The AM modulation circuit 14 receives and amplitude-modulates the PM RF signal RFPM using the AM signal VAM to provide a polar-modulated RF input signal RFAMPM to the PA stage 18, which amplifies the polar-modulated RF input signal RFAMPM to provide a polar-modulated RF output signal RFAMPMOUT. The AM power supply output signal VAMPSO may provide power for amplification to the PA stage 18. Generally, the polar-modulated RF input signal RFAMPM is one embodiment of the AM RF input signal RFAM and the polar-modulated RF output signal RFAMPMOUT is one embodiment of the AM RF output signal RFAMOUT. Alternate embodiments of the polar-modulated RF power amplifier circuit 30 may include at least one additional PA stage coupled in series with the PA stage 18.

Figure 7:
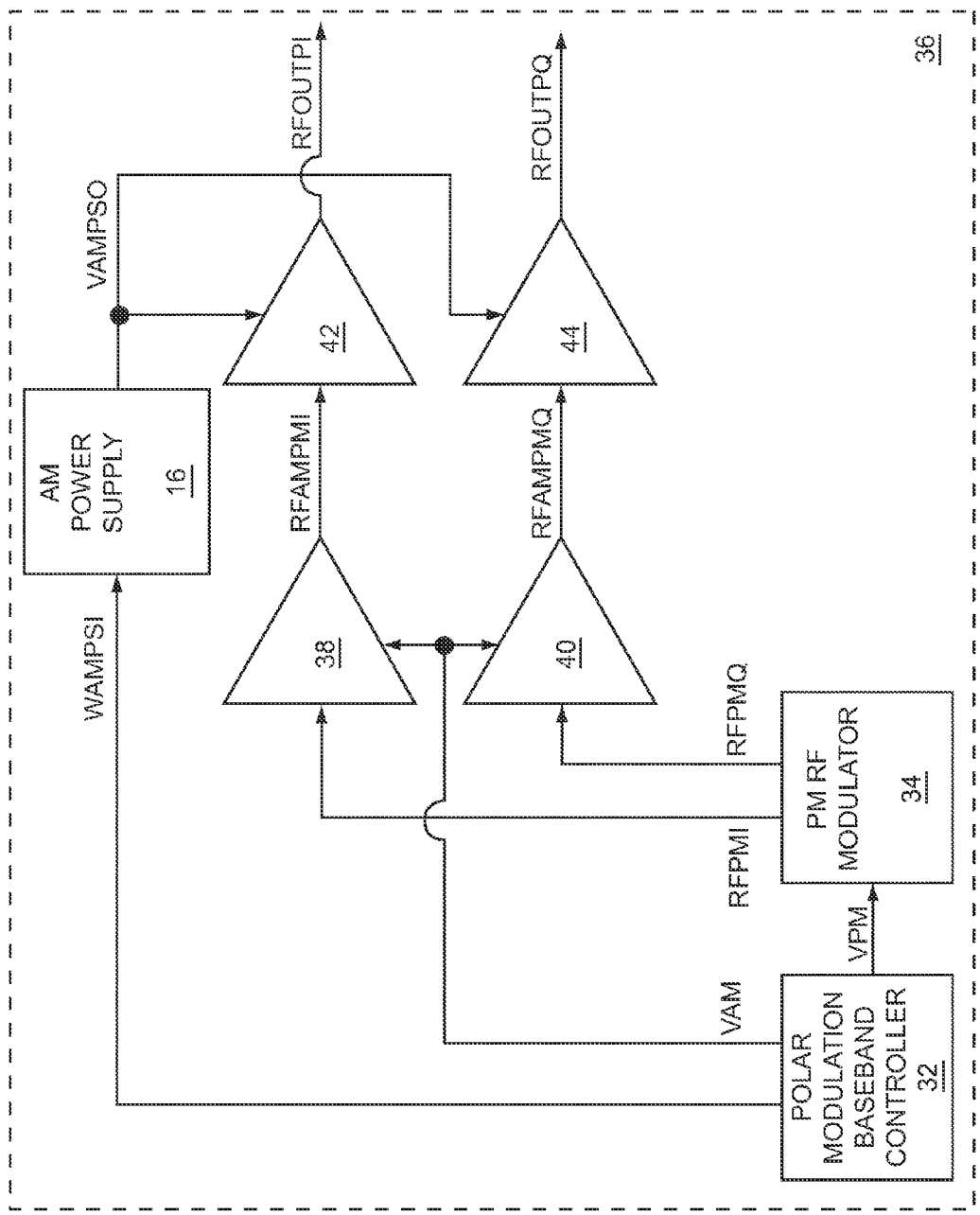
FIG. 7 shows a windowed polar-modulated quadrature RF power amplifier circuit, according to an additional embodiment of the present disclosure.

FIG. 7 shows a polar-modulated quadrature RF power amplifier circuit 36, according to one embodiment of the polar-modulated quadrature RF power amplifier circuit 36. The polar modulation baseband controller 32 provides the AM signal VAM to an in-phase AM modulation circuit 38 and a quadrature-phase AM modulation circuit 40, and provides the PM signal VPM to the PM RF modulator 34, which phase-modulates an RF carrier signal (not shown) using the PM signal VPM to provide an in-phase PM RF signal RFPMI to the in-phase AM modulation circuit 38 and a quadrature-phase PM RF signal RFPMQ to the quadrature-phase AM modulation circuit 40. The polar modulation baseband controller 32 provides the windowed AM power supply input signal WAMPSI to the AM power supply 16, which provides the AM power supply output signal VAMPSO based on the windowed AM power supply input signal WAMPSI.

The in-phase AM modulation circuit 38 receives and amplitude-modulates the in-phase PM RF signal RFPMI using the AM signal VAM to provide an in-phase polar-modulated RF input signal RFAMPMI to an in-phase PA stage 42, which amplifies the in-phase polar-modulated RF input signal RFAMPMI to provide an in-phase polar-modulated RF output signal RFOUTPI. The quadrature-phase AM modulation circuit 40 receives and amplitude-modulates the quadrature-phase PM RF signal RFPMQ using the AM signal VAM to provide a quadrature-phase polar-modulated RF input signal RFAMPMQ to a quadrature-phase PA stage 44, which amplifies the quadrature-phase polar-modulated RF input signal RFAMPMQ to provide a quadrature-phase polar-modulated RF output signal RFOUTPQ. The AM power supply output signal VAMPSO may provide power for amplification to the in-phase PA stage 42 and the quadrature-phase PA stage 44. The in-phase PM RF signal RFPMI may be of about equal amplitude to and phase-shifted from the quadrature-phase PM RF signal RFPMQ by about 90 degrees.

Generally, the in-phase polar-modulated RF input signal RFAMPMI is one embodiment of an in-phase AM RF input signal (not shown), the quadrature-phase polar-modulated RF input signal RFAMPMQ is one embodiment of a quadrature-phase AM RF input signal (not shown), the in-phase polar-modulated RF output signal RFOUTPI is one embodiment of an in-phase AM RF output signal (not shown), and the quadrature-phase polar-modulated RF output signal RFOUTPQ is one embodiment of a quadrature-phase AM RF output signal (not shown). Further, the in-phase AM RF input signal and the quadrature-phase AM RF input signal together form one embodiment of the AM RF input signal RFAM, and the in-phase AM RF output signal and the quadrature-phase AM RF output signal together form one embodiment of the AM RF output signal RFAMOUT. Alternate embodiments of the polar-modulated quadrature RF power amplifier circuit 36 may include at least one additional PA stage coupled in series with the in-phase PA stage 42 and may include at least one additional PA stage coupled in series with the quadrature-phase PA stage 44.

Figure 8:
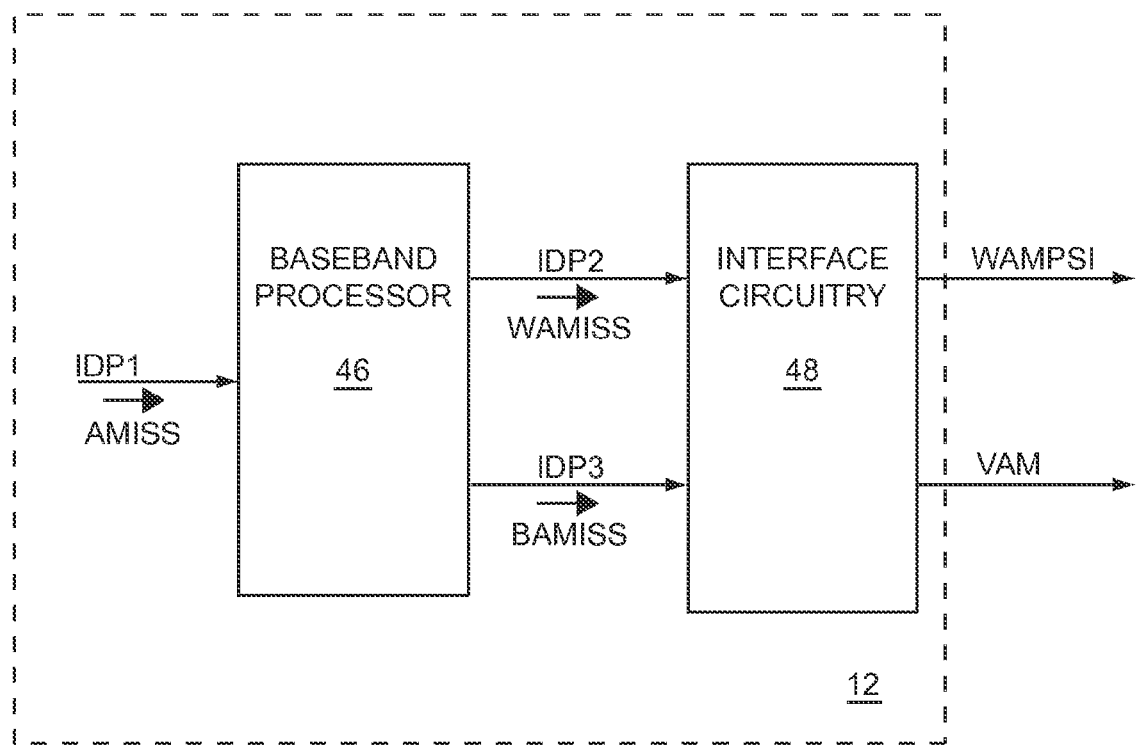
FIG. 8 shows details of an AM baseband controller illustrated in FIG. 5 according to one embodiment of the AM baseband controller.

FIG. 8 shows details of the AM baseband controller 12 illustrated in FIG. 5 according to one embodiment of the AM baseband controller 12. The AM baseband controller 12 includes a baseband processor 46 and interface circuitry 48. The baseband processor 46 receives a stream of AM input signal samples AMISS via a first internal data path IDP1 and creates a stream of windowed AM input signal samples WAMISS based on the stream of AM input signal samples AMISS. The baseband processor 46 provides the stream of windowed AM input signal samples WAMISS to the interface circuitry 48 via a second internal data path IDP2. Further, the baseband processor 46 time-arranges the stream of AM input signal samples AMISS to provide a stream of buffered AM input signal samples BAMISS to the interface circuitry 48 via a third internal data path IDP3. The interface circuitry 48 provides the windowed AM power supply input signal WAMPSI based on the stream of windowed AM input signal samples WAMISS and provides the AM signal VAM based on the stream of buffered AM input signal samples BAMISS. Since the stream of buffered AM input signal samples BAM- ISS is based on a time-arrangement of the stream of AM input signal samples AMISS, the timing of the windowed AM power supply input signal WAMPSI relative to the AM signal VAM is proper.

In one embodiment of the baseband processor 46, the windowing process is presented. The stream of AM input signal samples AMISS is divided into a stream of input windows and the stream of windowed AM input signal samples WAMISS is created from a stream of output windows. Each output window is created from a corresponding input window. Each input window includes N of the stream of AM input signal samples AMISS and each output window provides M of the stream of windowed AM input signal samples WAMISS, such that under at least certain operating conditions, N is greater than one and M is less than or equal to N. The windowed AM power supply input signal WAMPSI is provided using the stream of windowed AM input signal samples WAMISS.

In one exemplary embodiment of the baseband processor 46, N is a first fixed value under all operating conditions and M is a second fixed value under all operating conditions, such that the first fixed value is greater than one. In a first exemplary embodiment of the baseband processor 46, the first fixed value is three and the second fixed value may be one, two, or three. In a second exemplary embodiment of the baseband processor 46, the first fixed value is four and the second fixed value may be one, two, or three.

In an alternate exemplary embodiment of the baseband processor 46, N is variable and is based on values of the stream of AM input signal samples AMISS. In a third exemplary embodiment of the baseband processor 46, N is equal to one if the values of the stream of AM input signal samples AMISS are less than the first threshold 26 (FIG. 4) and N is greater than one of the values of the stream of AM input signal samples AMISS are greater than the first threshold 26. In a fourth exemplary embodiment of the baseband processor 46, N is either one, two, or three. In a fifth exemplary embodiment of the baseband processor 46, N is either one, two, three, or four.

In one embodiment of the baseband processor 46, all of the stream of windowed AM input signal samples WAMISS in each output window have a same value, which is based on the stream of AM input signal samples AMISS in the corresponding input window, such that each output window is adjacent to at least another output window. In one exemplary embodiment of the baseband processor 46, the same value in a given output window is about equal to a highest value of the stream of AM input signal samples AMISS in the corresponding input window. In an alternate exemplary embodiment of the baseband processor 46, the same value in a given output window is about equal to an average value of the stream of AM input signal samples AMISS in the corresponding input window plus a first constant. M may be equal to N, such that each input window is adjacent to at least another input window. Conversely, M may be less than N, such that each input window overlaps at least another input window.

In one embodiment of the baseband processor 46, a bandwidth of the windowed AM power supply input signal WAMPSI when N is equal to one may be greater than a bandwidth of the windowed AM power supply input signal WAMPSI when N is greater than one. In one exemplary embodiment of the baseband processor 46, N is selected based on a desired bandwidth of the windowed AM power supply input signal WAMPSI. The desired bandwidth of the windowed AM power supply input signal WAMPSI may be based on a bandwidth that enables any or all of the PA stage 18 (FIGS. 5 and 6), the in-phase PA stage 42 (FIG. 7), and the quadrature-phase PA stage 44 (FIG. 7) to meet linearity requirements of the PA stages 18, 42, 44.

In one embodiment of the baseband processor 46, N is selected based on an AM bandwidth of the AM RF input signal RFAM. For example, when the AM RF input signal RFAM is a 4G signal, such as a Long Term Evolution (LTE) signal, the AM bandwidth may be 1.4 megahertz (MHz), 3 MHz, 5 MHz, 10 MHz, 15 MHz, or 20 MHz; N may be selected to be one when the AM bandwidth is 1.4 MHz, 3 MHz, 5 MHz, such that the bandwidth of the windowed AM power supply input signal WAMPSI is not reduced. However, N may be selected to be three or four when the AM bandwidth is 10 MHz, 15 MHz, or 20 MHz, such that the bandwidth of the windowed AM power supply input signal WAMPSI is reduced to meet linearity requirements.

Figure 9:
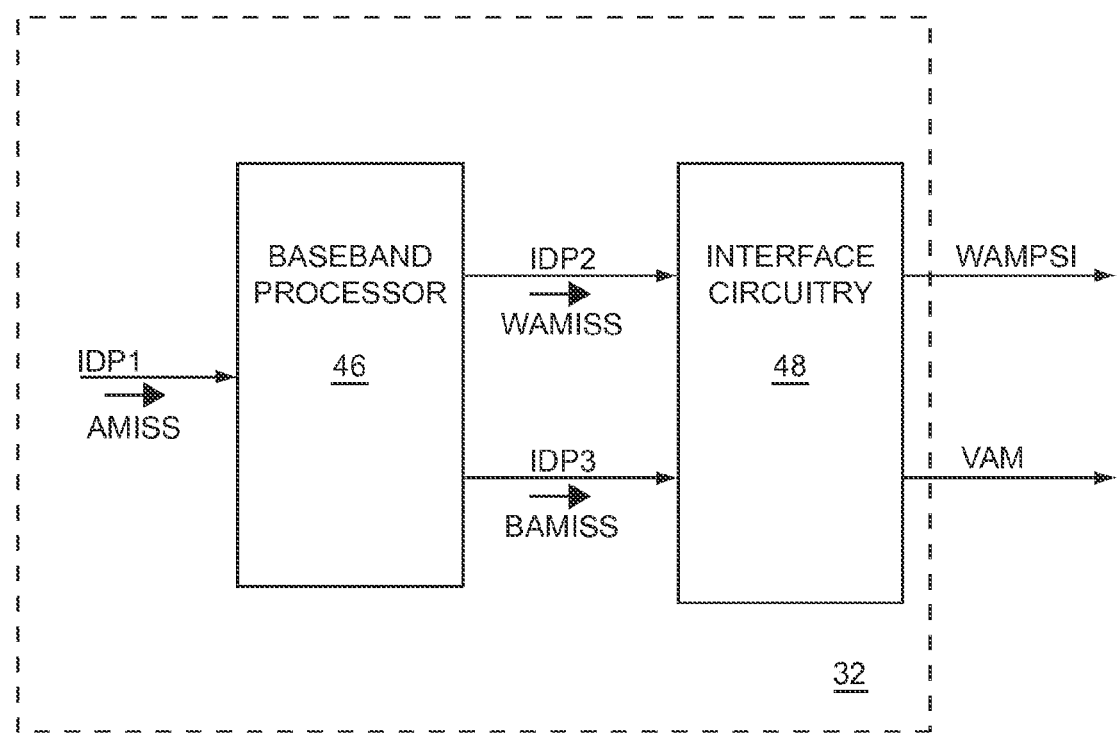
FIG. 9 shows details of a polar modulation baseband controller illustrated in FIGS. 6 and 7 according to one embodiment of the polar modulation baseband controller.

FIG. 9 shows details of the polar modulation baseband controller 32 illustrated in FIGS. 6 and 7 according to one embodiment of the polar modulation baseband controller 32. The details of the polar modulation baseband controller 32 illustrated in FIG. 9 are equivalent to the details of the AM baseband controller 12 illustrated in FIG. 8.

Figure 10:
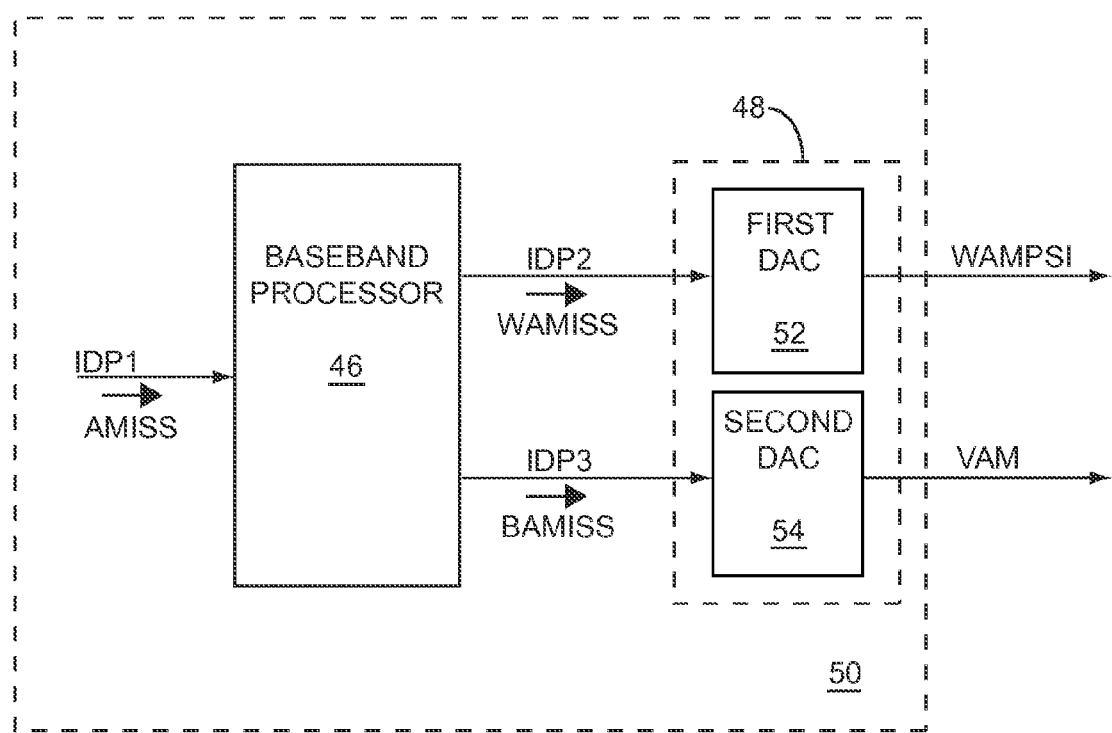
FIG. 10 shows details of a generic baseband controller according to one embodiment of the generic baseband controller.

FIG. 10 shows details of a generic baseband controller 50 according to one embodiment of the generic baseband controller 50. The generic baseband controller 50 may be equivalent to the AM baseband controller 12 or to the polar modulation baseband controller 32. As such, the details of the generic baseband controller 50 illustrated in FIG. 10 are based on the details of the AM baseband controller 12 and the polar modulation baseband controller 32 shown in FIGS. 8 and 9, respectively.

The interface circuitry 48 includes a first digital-to-analog converter (DAC) 52 and a second DAC 54. The first DAC 52 receives the stream of windowed AM input signal samples WAMISS via the second internal data path IDP2 and converts the windowed AM input signal samples WAMISS, which are in digital form, into the windowed AM power supply input signal WAMPSI, which is in analog form. The second DAC 54 receives the stream of buffered AM input signal samples BAMISS via the third internal data path IDP3 and converts the stream of buffered AM input signal samples BAMISS, which are in digital form, into the AM signal VAM, which is in analog form.

Figure 11:
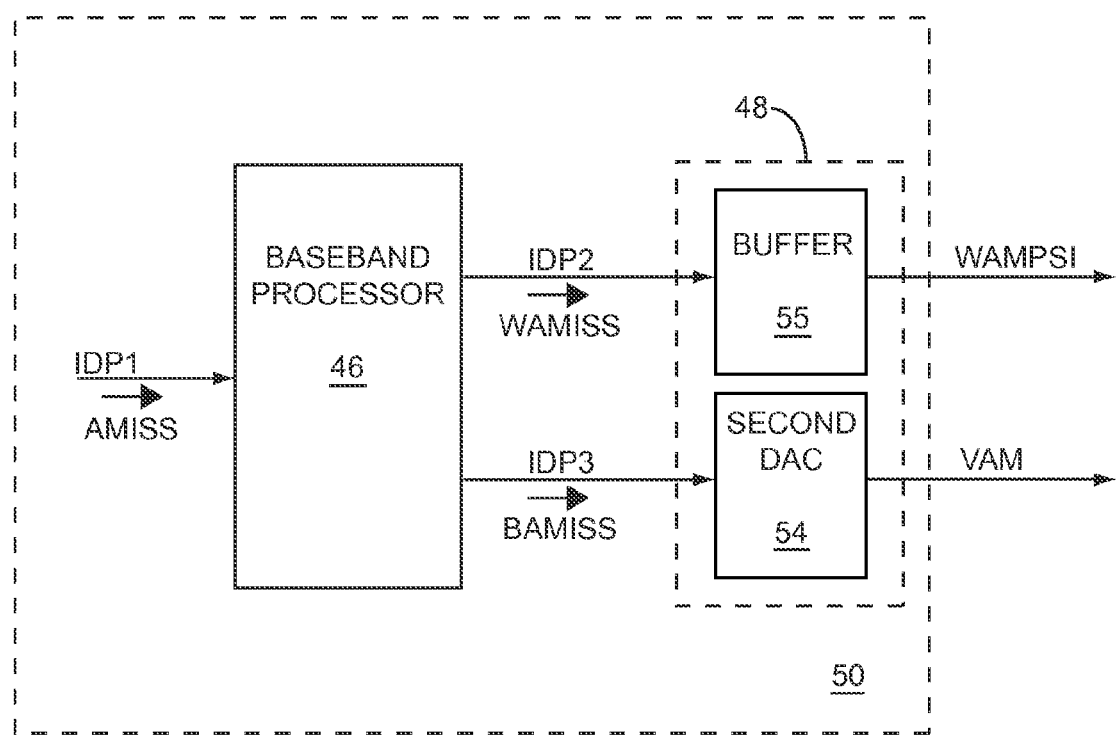
FIG. 11 shows details of the generic baseband controller according to an alternate embodiment of the generic baseband controller.

FIG. 11 shows details of the generic baseband controller 50 according to an alternate embodiment of the generic baseband controller 50. The generic baseband controller 50 illustrated in FIG. 11 is similar to the generic baseband controller 50 illustrated in FIG. 10, except in the generic baseband controller 50 illustrated in FIG. 11, the first DAC 52 is replaced with a buffer 55. Therefore, no digital-to-analog conversion of the stream of windowed AM input signal samples WAMISS to provide the windowed AM power supply input signal WAMPSI occurs. As a result, the windowed AM power supply input signal WAMPSI is a digital signal based on the stream of windowed AM input signal samples WAMISS.

Figure 12:
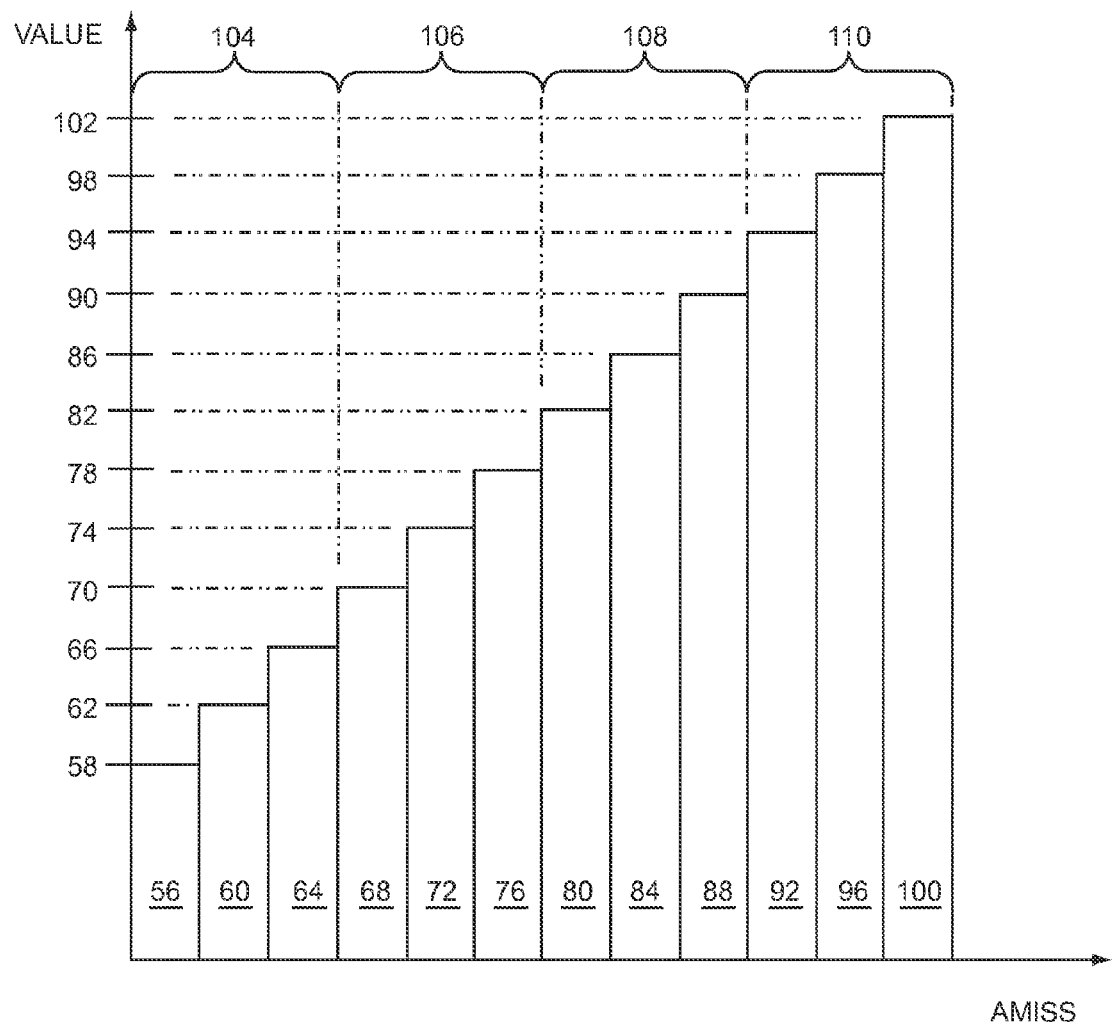
FIG. 12 is a graph showing details of windowing the stream of AM input signal samples illustrated in FIGS. 8, 9, 10, and 11 according to one embodiment of the windowing of the stream of AM input signal samples.

FIG. 12 is a graph showing details of input windowing the stream of AM input signal samples AMISS illustrated in FIGS. 8, 9, 10, and 11 according to one embodiment of the input windowing of the stream of AM input signal samples AMISS. The stream of AM input signal samples AMISS includes a first AM input signal sample 56 having a first value 58, a second AM input signal sample 60 having a second value 62, a third AM input signal sample 64 having a third value 66, a fourth AM input signal sample 68 having a fourth value 70, a fifth AM input signal sample 72 having a fifth value 74, a sixth AM input signal sample 76 having a sixth value 78, a seventh AM input signal sample 80 having a seventh value 82, an eighth AM input signal sample 84 having an eighth value 86, a ninth AM input signal sample 88 having a ninth value 90, a tenth AM input signal sample 92 having a tenth value 94, an eleventh AM input signal sample 96 having an eleventh value 98, and a twelfth AM input signal sample 100 having a twelfth value 102.

The stream of AM input signal samples AMISS is divided into a stream of input windows, which includes a first input window 104 having the first AM input signal sample 56, the second AM input signal sample 60, and the third AM input signal sample 64; a second input window 106 having the fourth AM input signal sample 68, the fifth AM input signal sample 72, and the sixth AM input signal sample 76; a third input window 108 having the seventh AM input signal sample 80, the eighth AM input signal sample 84, and the ninth AM input signal sample 88; and a fourth input window 110 having the tenth AM input signal sample 92, the eleventh AM input signal sample 96, and the twelfth AM input signal sample 100. As such, each of the input windows 104, 106, 108, 110 includes three of the stream of AM input signal samples AMISS. In general, each of the input windows 104, 106, 108, 110 includes N of the stream of AM input signal samples AMISS. Therefore, in the input windowing illustrated in FIG. 12, N is equal to three.

Figure 13:
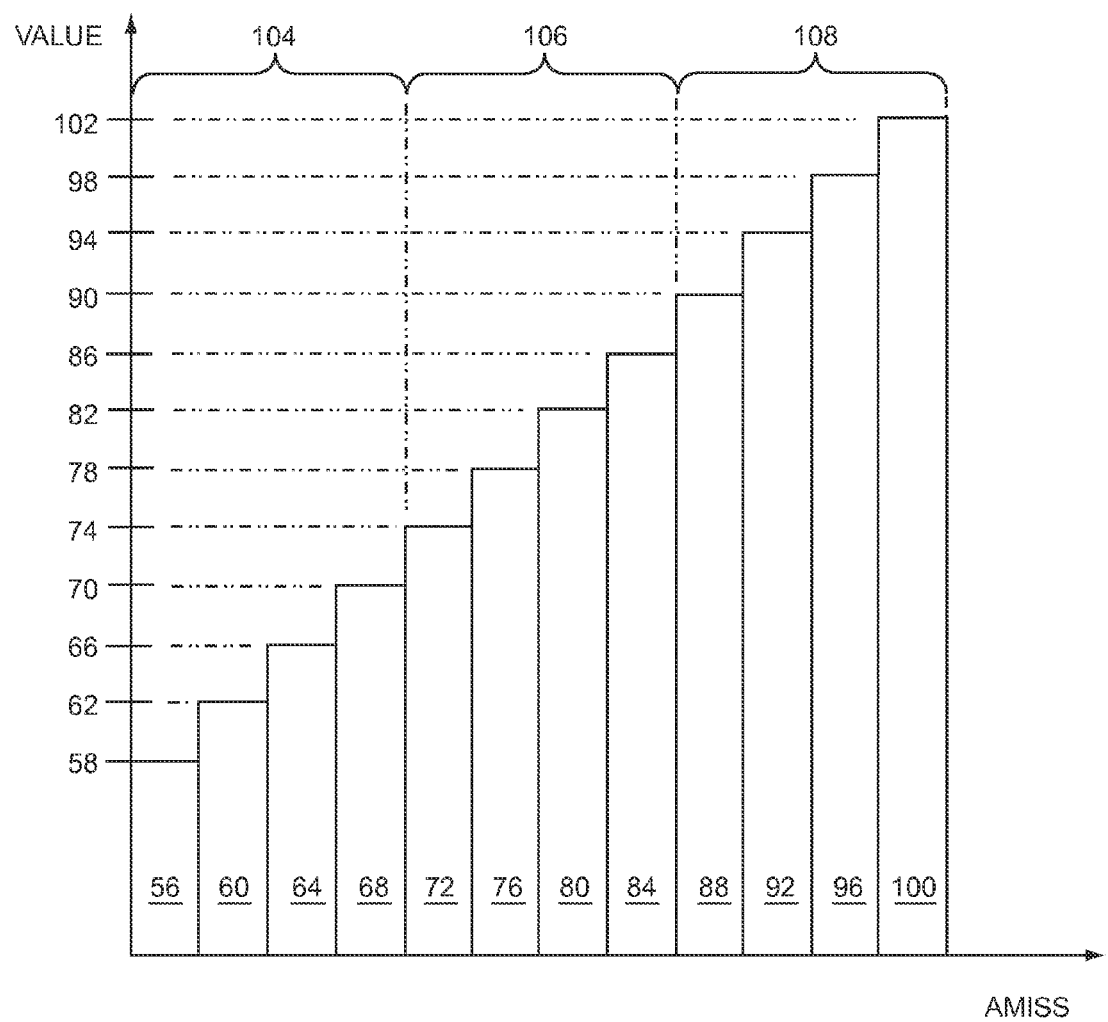
FIG. 13 is a graph showing details of windowing the stream of AM input signal samples illustrated in FIGS. 8, 9, 10, and 11 according to an alternate embodiment of the windowing of the stream of AM input signal samples.

FIG. 13 is a graph showing details of input windowing the stream of AM input signal samples AMISS illustrated in FIGS. 8, 9, 10, and 11 according to an alternate embodiment of the input windowing of the stream of AM input signal samples AMISS. The stream of AM input signal samples AMISS illustrated in FIG. 13 is similar to the stream of AM input signal samples AMISS illustrated in FIG. 12, except in the input windowing illustrated in FIG. 13, N is equal to four instead of three. Therefore, the stream of AM input signal samples AMISS is divided into a stream of input windows, which includes the first input window 104 having the first AM input signal sample 56, the second AM input signal sample 60, the third AM input signal sample 64, and the fourth AM input signal sample 68; the second input window 106 having the fifth AM input signal sample 72, the sixth AM input signal sample 76, the seventh AM input signal sample 80, and the eighth AM input signal sample 84; and the third input window 108 having the ninth AM input signal sample 88, the tenth AM input signal sample 92, the eleventh AM input signal sample 96, and the twelfth AM input signal sample 100. As such, each of the input windows 104, 106, 108 includes four of the stream of AM input signal samples AMISS.

Figure 14:
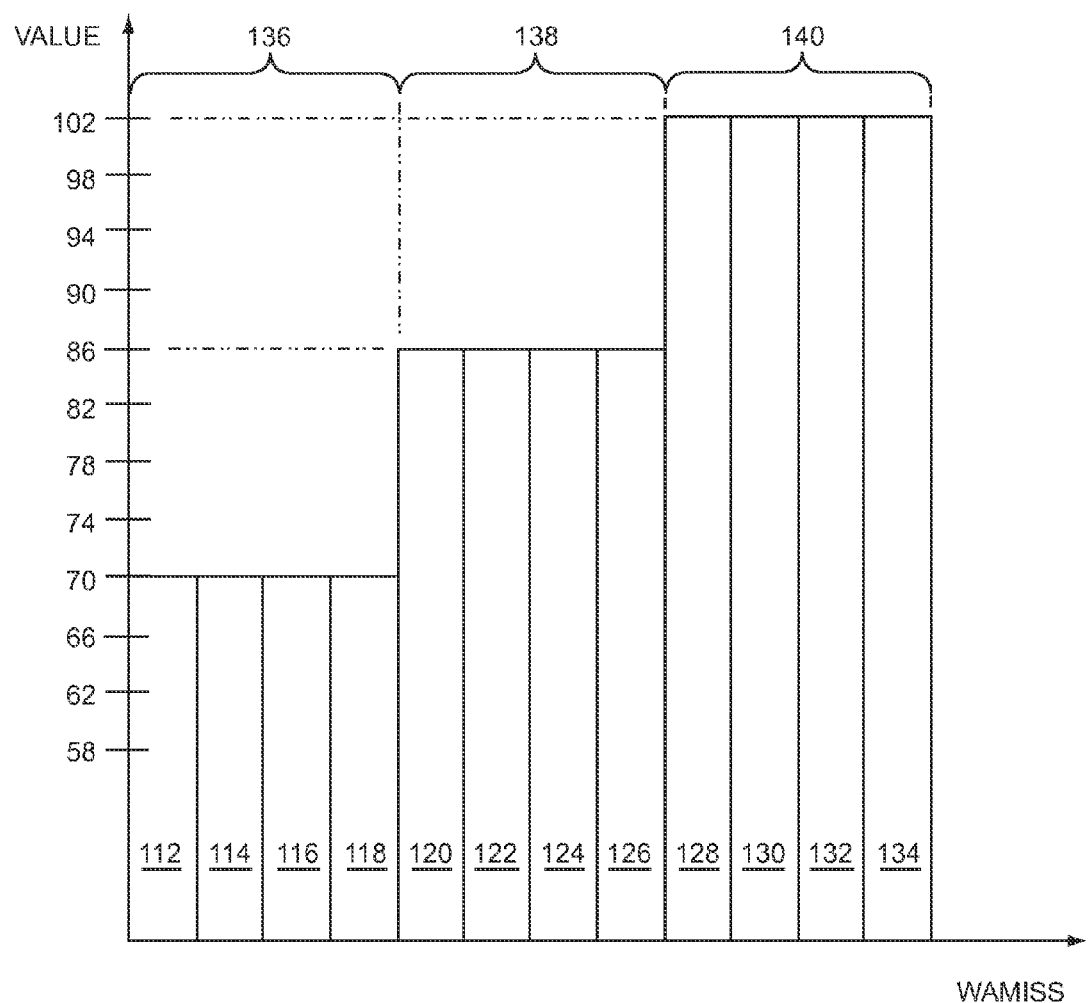
FIG. 14 is a graph showing details of windowing the stream of windowed AM input signal samples illustrated in FIGS. 8, 9, 10, and 11 according to one embodiment of the windowing of the stream of windowed AM input signal samples.

FIG. 14 is a graph showing details of windowing the stream of windowed AM input signal samples WAMISS illustrated in FIGS. 8, 9, 10, and 11 according to one embodiment of the windowing of the stream of windowed AM input signal samples WAMISS. In the embodiment shown, M is equal to four. Since N is also equal to four, the input windows 104, 106, 108 are adjacent to one another as shown in FIG. 13. The stream of windowed AM input signal samples WAMISS is created from a stream of output windows, which correspond to the stream of input windows 104, 106, 108 illustrated in FIG. 13. Specifically, the stream of windowed AM input signal samples WAMISS includes a first windowed AM input signal sample 112, a second windowed AM input signal sample 114, a third windowed AM input signal sample 116, a fourth windowed AM input signal sample 118, a fifth windowed AM input signal sample 120, a sixth windowed AM input signal sample 122, a seventh windowed AM input signal sample 124, an eighth windowed AM input signal sample 126, a ninth windowed AM input signal sample 128, a tenth windowed AM input signal sample 130, a eleventh windowed AM input signal sample 132, and a twelfth windowed AM input signal sample 134.

A first output window 136 corresponds with the first input window 104, a second output window 138 corresponds with the second input window 106, and a third output window 140 corresponds with the third input window 108. In general, each of the output windows 136, 138, 140 is created from a corresponding to one of the input windows 104, 106, 108, such that each of the input windows 104, 106, 108 includes N of the stream of AM input signal samples AMISS and each of the output windows 136, 138, 140 provides M of the stream of windowed AM input signal samples WAMISS. All of the stream of windowed AM input signal samples WAMISS in each of the output windows 136, 138, 140 have the same value, which is based on the stream of AM input signal samples AMISS in the corresponding one of the input windows 104, 106, 108. In the embodiment illustrated in FIG. 14, N is equal to four, M is equal to four, and the value of the windowed AM input signal samples WAMISS in each of the output windows 136, 138, 140 is the same value and is about equal to the highest value of the stream of AM input signal samples AMISS in the corresponding one of the input windows 104, 106, 108.

As such, the first output window 136 corresponds with the first input window 104 and provides the first windowed AM input signal sample 112, the second windowed AM input signal sample 114, the third windowed AM input signal sample 116, and the fourth windowed AM input signal sample 118. Since the highest value in the first input window 104 is the fourth value 70, the value of all of the stream of windowed AM input signal samples WAMISS provided by the first output window 136 is about equal to the fourth value 70.

Similarly, the second output window 138 corresponds with the second input window 106 and provides the fifth windowed AM input signal sample 120, the sixth windowed AM input signal sample 122, the seventh windowed AM input signal sample 124, and the eighth windowed AM input signal sample 126. Since the highest value in the second input window 106 is the eighth value 86, the value of all of the stream of windowed AM input signal samples WAMISS provided by the second output window 138 is about equal to the eighth value 86.

Further, the third output window 140 corresponds with the third input window 108 and provides the ninth windowed AM input signal sample 128, the tenth windowed AM input signal sample 130, the eleventh windowed AM input signal sample 132, and the twelfth windowed AM input signal sample 134. Since the highest value in the third input window 108 is the twelfth value 102, the value of all of the stream of windowed AM input signal samples WAMISS provided by the third output window 140 is about equal to the twelfth value 102.

Figure 15:
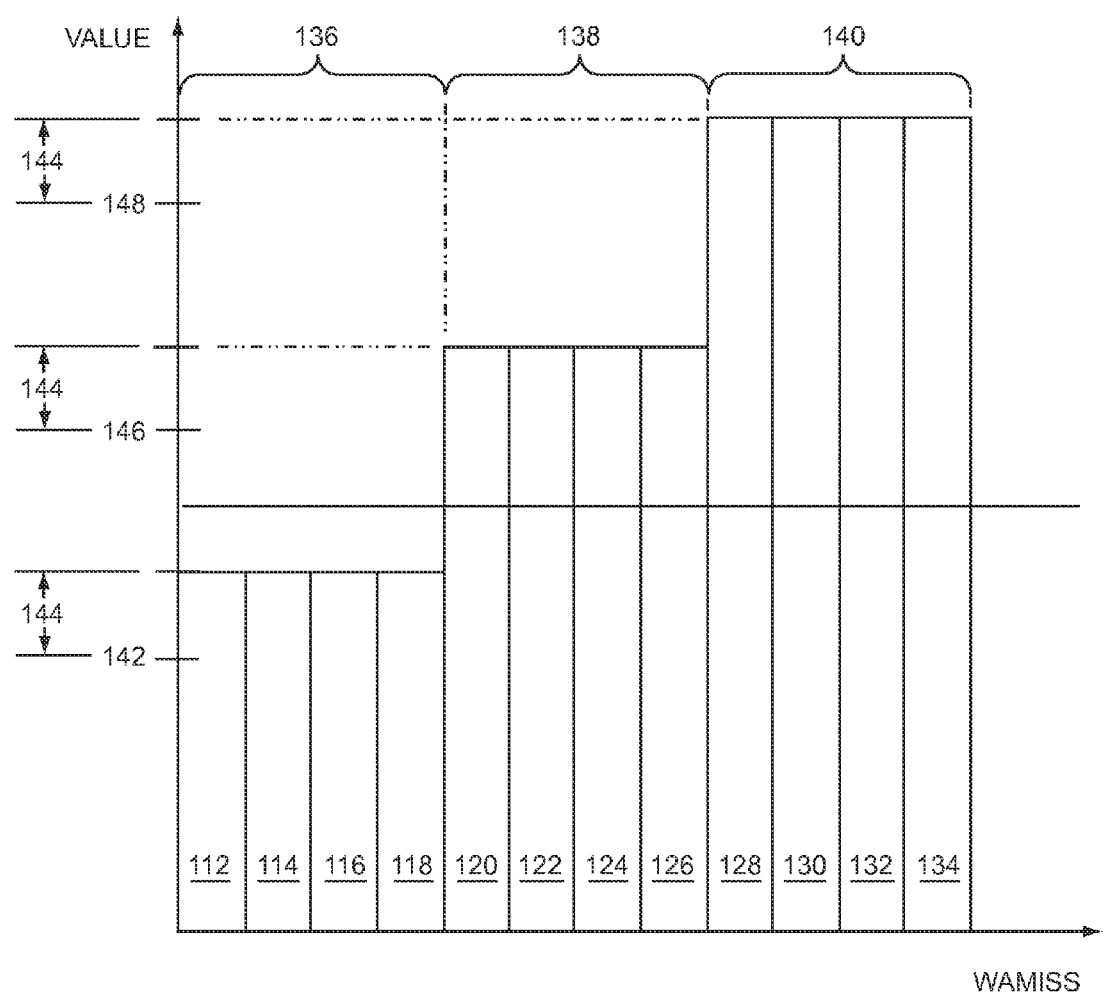
FIG. 15 is a graph showing details of windowing the stream of windowed AM input signal samples illustrated in FIGS. 8, 9, 10, and 11 according to an alternate embodiment of the windowing of the stream of windowed AM input signal samples.

FIG. 15 is a graph showing details of windowing the stream of windowed AM input signal samples WAMISS illustrated in FIGS. 8, 9, 10, and 11 according to an alternate embodiment of the windowing of the stream of windowed AM input signal samples WAMISS. The windowing of the stream of windowed AM input signal samples WAMISS illustrated in FIG. 15 is similar to the windowing of the stream of windowed AM input signal samples WAMISS illustrated in FIG. 14, except in the windowing of the stream of windowed AM input signal samples WAMISS. The values of the stream of windowed AM input signal samples WAMISS are determined in a different manner. In the stream of windowed AM input signal samples WAMISS illustrated in FIG. 14, the value of the windowed AM input signal samples WAMISS in each of the output windows 136, 138, 140 is the same value and is about equal to the highest value of the stream of AM input signal samples AMISS in the corresponding one of the input windows 104, 106, 108. However, in the stream of windowed AM input signal samples WAMISS illustrated in FIG. 15, the value of the windowed AM input signal samples WAMISS in each of the output windows 136, 138, 140 is the same value and is about equal to the average value of the stream of AM input signal samples AMISS in the corresponding one of the input windows 104, 106, 108 plus a first constant.

As such, the first output window 136 corresponds with the first input window 104 and provides the first windowed AM input signal sample 112, the second windowed AM input signal sample 114, the third windowed AM input signal sample 116, and the fourth windowed AM input signal sample 118. Since the average value in the first input window 104 is a first average window value 142, the value of all of the stream of windowed AM input signal samples WAMISS provided by the first output window 136 is about equal to the first average window value 142 plus a first constant 144.

Similarly, the second output window 138 corresponds with the second input window 106 and provides the fifth windowed AM input signal sample 120, the sixth windowed AM input signal sample 122, the seventh windowed AM input signal sample 124, and the eighth windowed AM input signal sample 126. Since the average value in the second input window 106 is the second average window value 146, the value of all of the stream of windowed AM input signal samples WAMISS provided by the second output window 138 is about equal to the second average window value 146 plus the first constant 144.

Further, the third output window 140 corresponds with the third input window 108 and provides the ninth windowed AM input signal sample 128, the tenth windowed AM input signal sample 130, the eleventh windowed AM input signal sample 132, and the twelfth windowed AM input signal sample 134. Since the average value in the third input window 108 is the third average window value 148, the value of all of the stream of windowed AM input signal samples WAMISS provided by the third output window 140 is about equal to the third average window value 148 plus the first constant 144.

Figure 16:
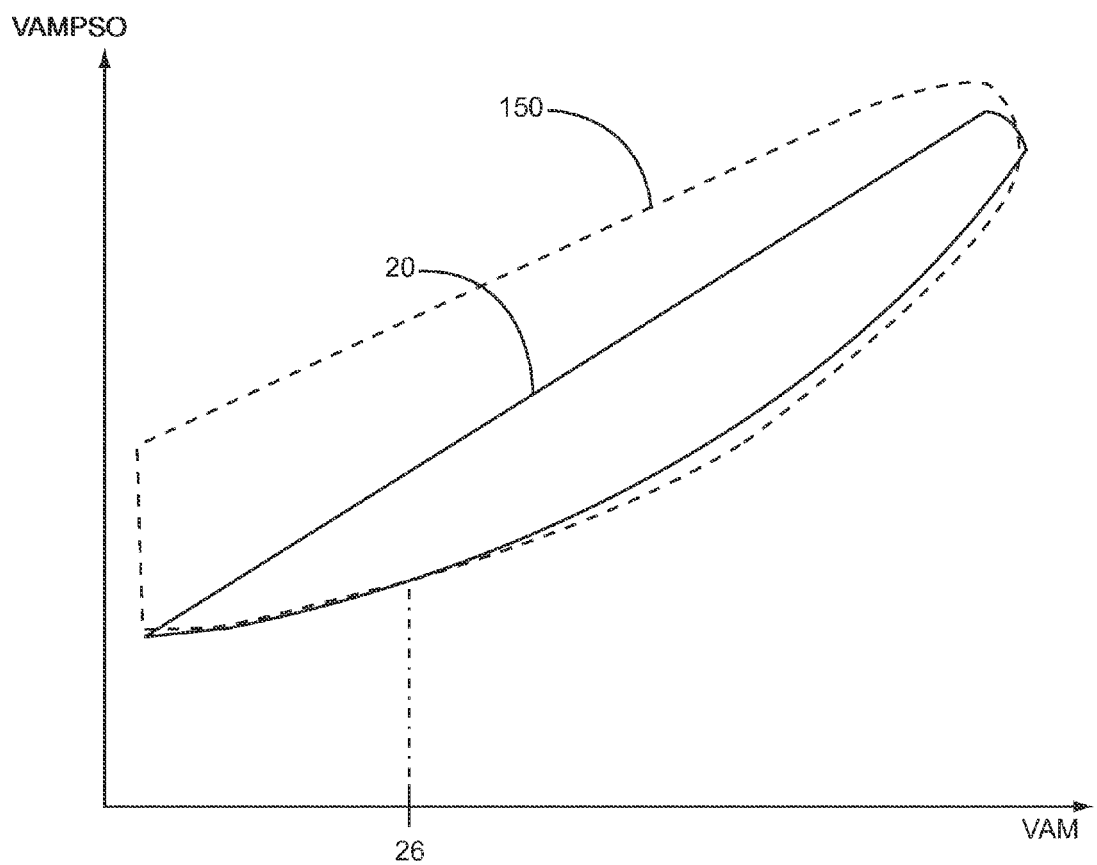
FIG. 16 is a graph showing simulation results of the AM power supply output signal versus the AM signal when the filtering bandwidth provided by the AM power supply is equal to two megahertz and a window sample size is equal to three, according to exemplary embodiments of the windowed RF power amplifier circuits illustrated in FIGS. 5, 6, and 7.

FIG. 16 is a graph showing simulation results of the AM power supply output signal VAMPSO versus the AM signal VAM when the filtering bandwidth provided by the AM power supply 16 is equal to two megahertz and a window sample size is equal to three, according to exemplary embodiments of the windowed RF power amplifier circuits 28, 30, 36 illustrated in FIGS. 5, 6, and 7 using the WCDMA HSUPA GTC3 test signal. As a result, the graph illustrated in FIG. 16 may be represented as a third distribution 150, as shown. The first distribution 20 is shown for reference. When comparing the third distribution 150 to the second distribution 22 shown in FIG. 4, the deficiency zones 24 (FIG. 4) have been almost eliminated. As a result, by using windowing, the bandwidth of the AM power supply 16 may be reduced from about seven megahertz to about two megahertz while continuing to largely meet linearity requirements. It should be noted that while linearity was largely preserved, delay dispersion increased, which may reduce efficiency.

Figure 17:
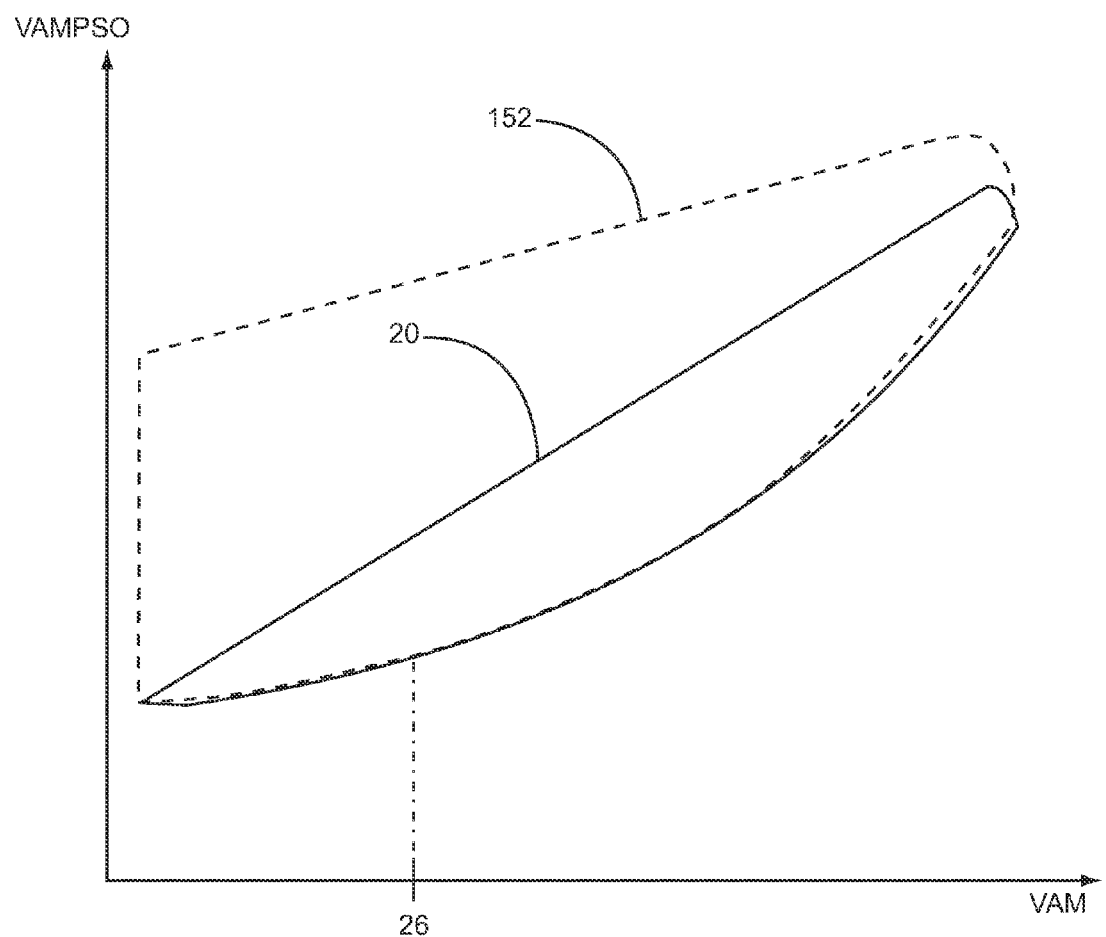
FIG. 17 is a graph showing simulation results of the AM power supply output signal versus the AM signal when the filtering bandwidth provided by the AM power supply is equal to two megahertz and a window sample size is equal to four, according to alternate embodiments of the windowed RF power amplifier circuits illustrated in FIGS. 5, 6, and 7.

FIG. 17 is a graph showing simulation results of the AM power supply output signal VAMPSO versus the AM signal VAM when the filtering bandwidth provided by the AM power supply 16 is equal to two megahertz and a window sample size is equal to four, according to alternate embodiments of the windowed RF power amplifier circuits 28, 30, 36 illustrated in FIGS. 5, 6, and 7 using the WCDMA HSUPA GTC3 test signal. As a result, the graph illustrated in FIG. 17 may be represented as a fourth distribution 152, as shown. The first distribution 20 is shown for reference. When comparing the fourth distribution 152 to the second distribution 22 shown in FIG. 4, the deficiency zones 24 (FIG. 4) have been completely eliminated. As a result, by using windowing, the bandwidth of the AM power supply 16 may be reduced from about seven megahertz to about two megahertz while continuing to meet linearity requirements. It should be noted that while linearity was preserved, delay dispersion further increased, which may further reduce efficiency.

Figure 18:
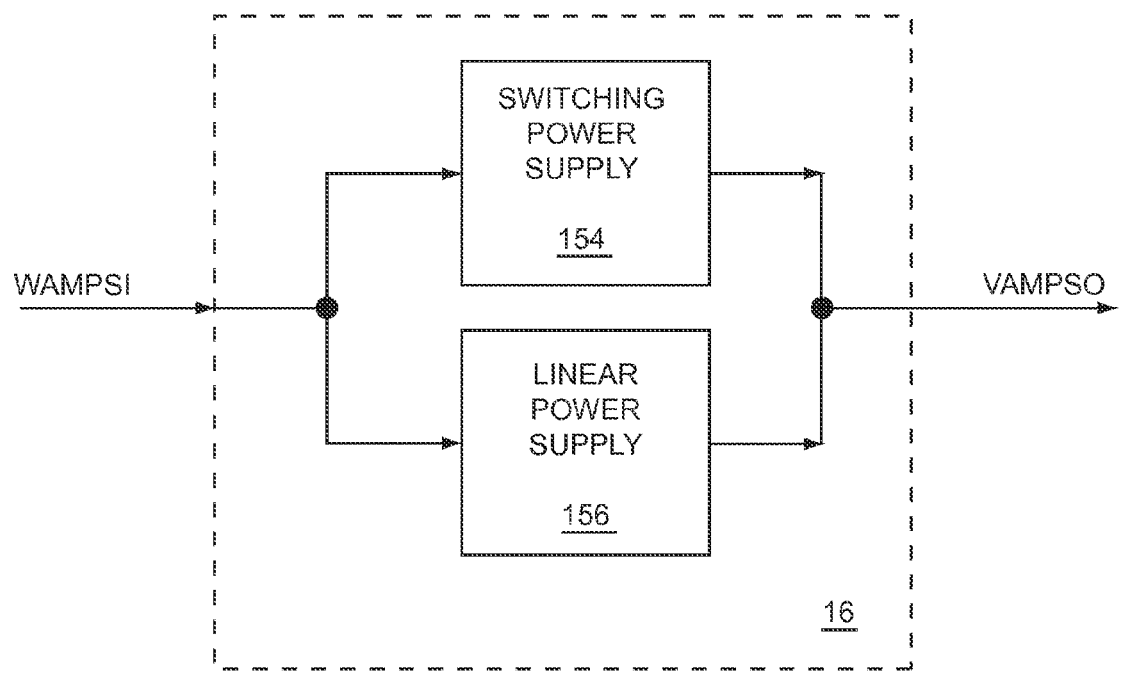
FIG. 18 shows details of an AM power supply illustrated in FIGS. 5, 6, and 7 according to one embodiment of the AM power supply.

FIG. 18 shows details of the AM power supply 16 illustrated in FIGS. 5, 6, and 7 according to one embodiment of the AM power supply 16. To meet bandwidth requirements and to maximize efficiency, the AM power supply 16 may include a switching power supply 154 and a linear power supply 156. The switching power supply 154 may provide high efficiency but have limited bandwidth, whereas the linear power supply 156 may provide greater bandwidth but have lower efficiency than the switching power supply 154. In an exemplary embodiment of the present invention, the bandwidth of the linear power supply 156 is at least two times the bandwidth of the switching power supply 154. In alternate embodiments of the AM power supply 16, either the switching power supply 154 or the linear power supply 156 may be omitted.

Figure 19:
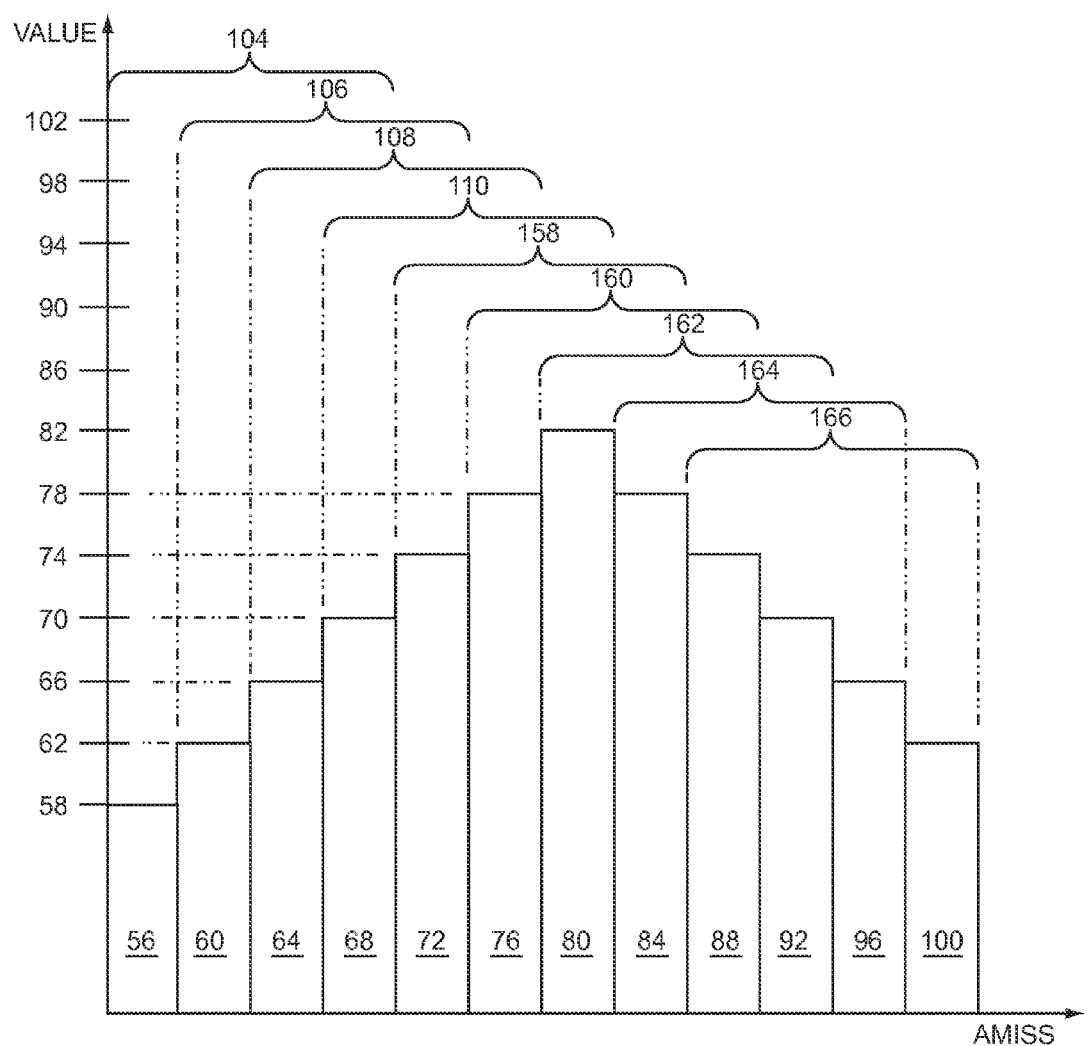
FIG. 19 is a graph showing details of input windowing the stream of AM input signal samples illustrated in FIGS. 8, 9, 10, and 11 according to an one embodiment of the input windowing of the stream of AM input signal samples.

FIG. 19 is a graph showing details of input windowing the stream of AM input signal samples AMISS illustrated in FIGS. 8, 9, 10, and 11 according to an one embodiment of the input windowing of the stream of AM input signal samples AMISS. The stream of AM input signal samples AMISS illustrated in FIG. 19 is similar to the stream of AM input signal samples AMISS illustrated in FIG. 13, except in the input windowing illustrated in FIG. 19, N is equal to four and M is equal to one. As such, the input windows in the stream of input windows are overlapped, as shown. Specifically, the stream of AM input signal samples AMISS is divided into the stream of input windows, which includes the first input window 104, the second input window 106; the third input window 108, the fourth input window 110, a fifth input window 158, a sixth input window 160, a seventh input window 162, an eighth input window 164, and a ninth input window 166. Since N is equal to four, each of the input windows 104, 106, 108, 110, 158, 160, 162, 164, 166 includes four of the stream of AM input signal samples AMISS. Since M is equal to one, each of the input windows 104, 106, 108, 110, 158, 160, 162, 164, 166 overlaps each of its two adjacent input windows by three of the stream of AM input signal samples AMISS.

Figure 20:
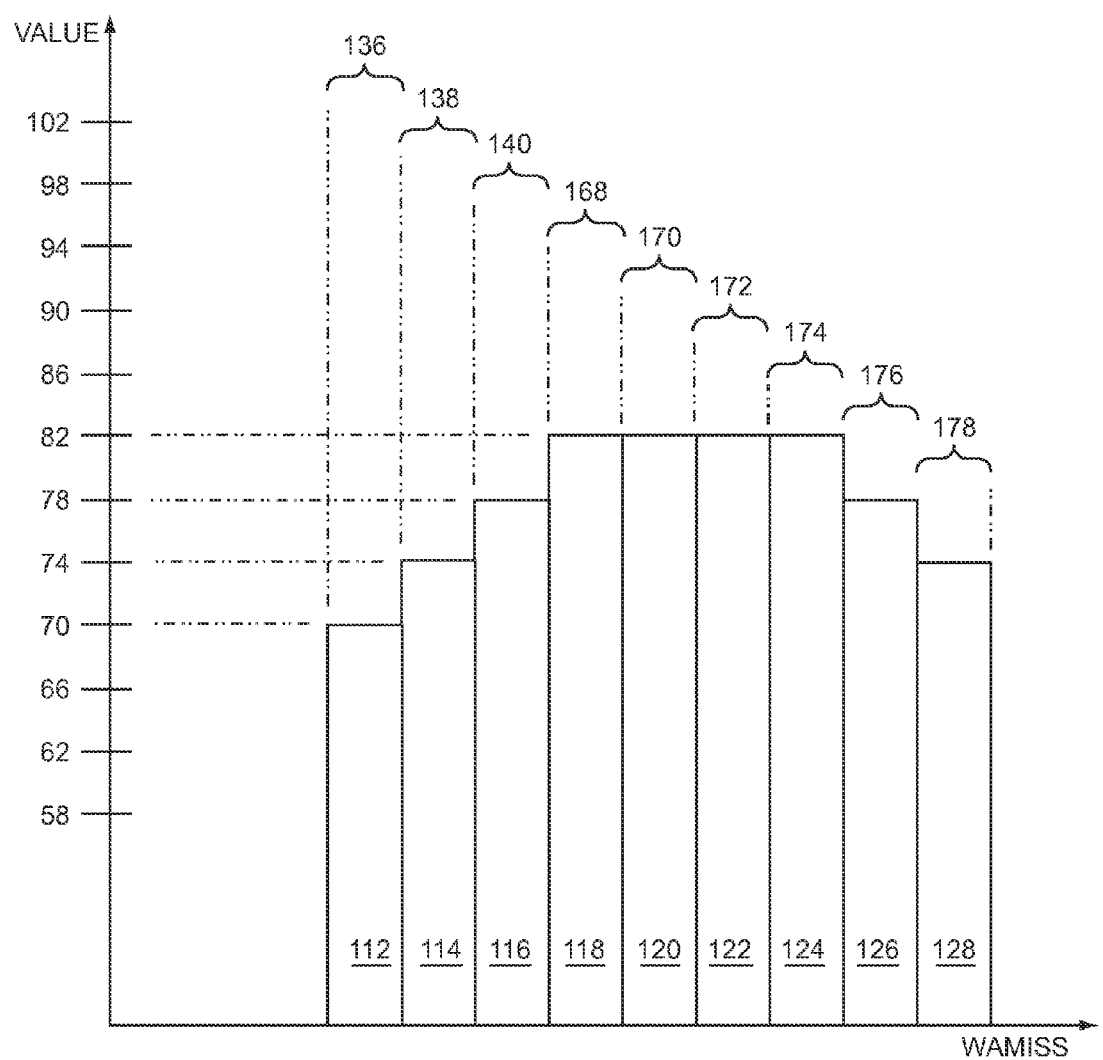
FIG. 20 is a graph showing details of windowing the stream of windowed AM input signal samples illustrated in FIGS. 8, 9, 10, and 11 according to one embodiment of the windowing of the stream of windowed AM input signal samples.

FIG. 20 is a graph showing details of windowing the stream of windowed AM input signal samples WAMISS illustrated in FIGS. 8, 9, 10, and 11 according to one embodiment of the windowing of the stream of windowed AM input signal samples WAMISS. The stream of windowed AM input signal samples WAMISS illustrated in FIG. 20 is similar to the stream of windowed AM input signal samples AMISS illustrated in FIG. 14, except in the output windowing illustrated in FIG. 20, N is equal to four and M is equal to one. Since M is equal to one, each output window provides only one of the stream of windowed AM input signal samples WAMISS. The stream of windowed AM input signal samples WAMISS is created from the stream of output windows, which correspond to the stream of input windows 104, 106, 108, 110, 158, 160, 162, 164, 166 illustrated in FIG. 19.

The first output window 136 corresponds with the first input window 104, the second output window 138 corresponds with the second input window 106, the third output window 140 corresponds with the third input window 108, a fourth output window 168 corresponds with the fourth input window 110, a fifth output window 170 corresponds with the fifth input window 158, a sixth output window 172 corresponds with the sixth input window 160, a seventh output window 174 corresponds with the seventh input window 162, an eighth output window 176 corresponds with the eighth input window 164, and a ninth output window 178 corresponds with the ninth input window 166. In the embodiment illustrated in FIG. 20, the value of the windowed AM input signal sample WAMISS in each of the output windows 136, 138, 140, 168, 170, 172, 174, 176, 178 is about equal to the highest value of the stream of AM input signal samples AMISS in the corresponding one of the input windows 104, 106, 108 110, 158, 160, 162, 164, 166.

The stream of AM input signal samples AMISS illustrated in FIG. 19 shows a triangle wave with a peak. However, after windowing, the corresponding stream of windowed AM input signal samples WAMISS illustrated in FIG. 20 shows that the peak has been flattened, thereby reducing the bandwidth of the windowed AM power supply input signal WAMPSI, as shown.

Figure 21:
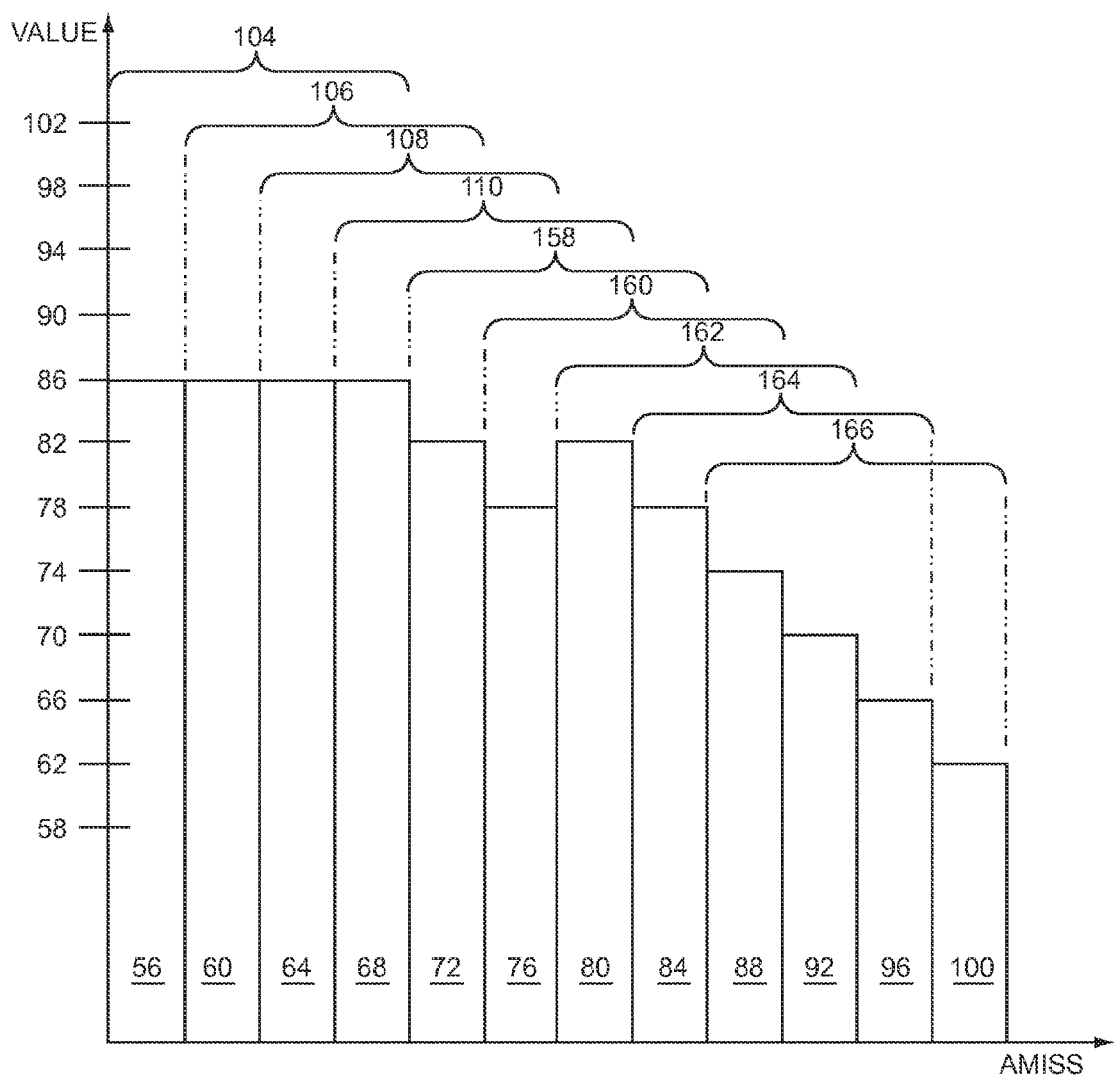
FIG. 21 is a graph showing details of input windowing the stream of AM input signal samples illustrated in FIGS. 8, 9, 10, and 11 according to an alternate embodiment of the input windowing of the stream of AM input signal samples.

FIG. 21 is a graph showing details of input windowing the stream of AM input signal samples AMISS illustrated in FIGS. 8, 9, 10, and 11 according to an alternate embodiment of the input windowing of the stream of AM input signal samples AMISS. The stream of AM input signal samples AMISS illustrated in FIG. 21 is similar to the stream of AM input signal samples AMISS illustrated in FIG. 19, except in the input windowing illustrated in FIG. 21, the waveshape provided by stream of AM input signal samples AMISS has a valley and a peak, as shown.

Figure 22:
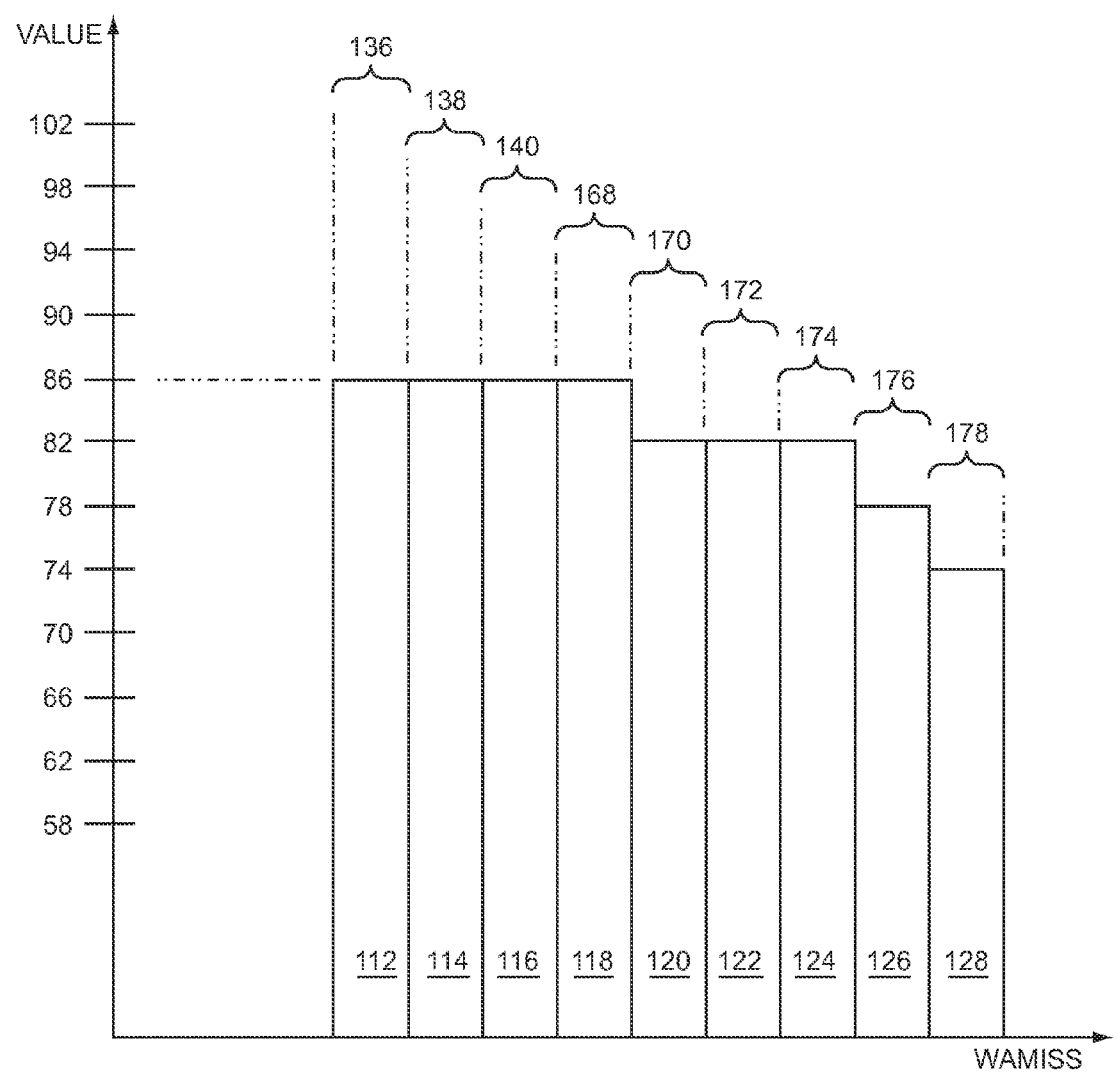
FIG. 22 is a graph showing details of windowing the stream of windowed AM input signal samples illustrated in FIGS. 8, 9, 10, and 11 according to an alternate embodiment of the windowing of the stream of windowed AM input signal samples.

FIG. 22 is a graph showing details of windowing the stream of windowed AM input signal samples WAMISS illustrated in FIGS. 8, 9, 10, and 11 according to an alternate embodiment of the windowing of the stream of windowed AM input signal samples WAMISS. The stream of windowed AM input signal samples WAMISS illustrated in FIG. 22 is similar to the stream of windowed AM input signal samples AMISS illustrated in FIG. 20, except the output windowing illustrated in FIG. 22 shows that the valley and the peak have been removed, thereby reducing the bandwidth of the windowed AM power supply input signal WAMPSI, as shown.

Some of the circuitry previously described may use discrete circuitry, integrated circuitry, programmable circuitry, non-volatile circuitry, volatile circuitry, software executing instructions on computing hardware, firmware executing instructions on computing hardware, the like, or any combination thereof. The computing hardware may include mainframes, micro-processors, micro-controllers, DSPs, the like, or any combination thereof.

None of the embodiments of the present disclosure are intended to limit the scope of any other embodiment of the present disclosure. Any or all of any embodiment of the present disclosure may be combined with any or all of any other embodiment of the present disclosure to create new embodiments of the present disclosure.

Those skilled in the art will recognize improvements and modifications to the preferred embodiments of the present disclosure. All such improvements and modifications are considered within the scope of the concepts disclosed herein and the claims that follow.

What is claimed is:

1. Radio frequency (RF) circuitry comprising:
a baseband controller adapted to:
window a stream of amplitude modulation input signal (AMIS) samples to create a stream of windowed AMIS samples, such that:
the stream of AMIS samples is divided into a stream of input windows and the stream of windowed AMIS samples is created from a stream of output windows;
each output window is created from a corresponding input window; and
each input window includes N of the stream of AMIS samples and each output window provides M of the stream of windowed AMIS samples, such that under at least certain operating conditions, N is greater than one, and M is less than or equal to N; and
provide a windowed amplitude modulation power supply input signal (WAMPSIS) using the stream of windowed AMIS samples;
an amplitude modulation (AM) power supply adapted to provide an AM power supply output signal based on the WAMPSIS; and
a power amplifier stage adapted to:
receive and amplify an AM RF input signal to provide an AM RF output signal; and
use the AM power supply output signal to provide power for amplification.

2. The RF circuitry of claim 1 wherein N is a first fixed value under all operating conditions and M is a second fixed value under all operating conditions, such that the first fixed value is greater than one.

3. The RF circuitry of claim 2 wherein the first fixed value is three and the second fixed value is one.

4. The RF circuitry of claim 2 wherein the first fixed value is four and the second fixed value is one.

5. The RF circuitry of claim 1 wherein N is variable and based on values of the stream of AMIS samples.

6. The RF circuitry of claim 5 wherein N is equal to one if the values of the stream of AMIS samples are less than a first threshold and N is greater than one if the values of the stream of AMIS samples are greater than the first threshold.

7. The RF circuitry of claim 5 wherein N is selected from a group consisting of one, two, and three.

8. The RF circuitry of claim 5 wherein N is selected from a group consisting of one, two, three, and four.

9. The RF circuitry of claim 1 wherein all of the stream of windowed AMIS samples in each output window have a same value, which is based on the stream of windowed AMIS samples in the corresponding input window, and each output window is adjacent to at least another output window.

10. The RF circuitry of claim 9 wherein the same value is about equal to a highest value of the stream of windowed AMIS samples in the corresponding input window.

11. The RF circuitry of claim 9 wherein the same value is about equal to an average value of the stream of windowed AMIS samples in the corresponding input window plus a first constant.

12. The RF circuitry of claim 9 wherein M is equal to N and each input window is adjacent to at least another input window.

13. The RF circuitry of claim 9 wherein M is less than N and each input window overlaps at least another input window.

14. The RF circuitry of claim 1 wherein a bandwidth of the WAMPSIS when N is equal to one is greater than a bandwidth of the WAMPSIS when N is greater than one.

15. The RF circuitry of claim 1 wherein N is selected based on a desired bandwidth of the WAMPSIS.

16. The RF circuitry of claim 15 wherein the desired bandwidth of the WAMPSIS is based on a bandwidth of the WAMPSIS that enables the power amplifier stage to meet a linearity requirement of the power amplifier stage.

17. The RF circuitry of claim 1 wherein N is selected based on an AM bandwidth of the AM RF input signal.

18. The RF circuitry of claim 1 wherein the AM power supply comprises a switching power supply.

19. The RF circuitry of claim 18 wherein the AM power supply further comprises a linear power supply.

20. The RF circuitry of claim 1 wherein the AM RF input signal is a polar-modulated RF input signal and the AM RF output signal is a polar-modulated RF output signal.

21. The RF circuitry of claim 1 wherein:
the AM RF input signal comprises an in-phase AM RF input signal and a quadrature-phase AM RF input signal;
the AM RF output signal comprises an in-phase AM RF output signal and a quadrature-phase AM RF output signal;
the power amplifier stage comprises:
an in-phase power amplifier stage adapted to receive and amplify the in-phase AM RF input signal to provide the in-phase AM RF output signal; and
a quadrature-phase power amplifier stage adapted to receive and amplify the quadrature-phase AM RF input signal to provide the quadrature-phase AM RF output signal.

22. The RF circuitry of claim 21 wherein:
the in-phase AM RF input signal is an in-phase polar-modulated RF input signal;
the in-phase AM RF output signal is an in-phase polar-modulated RF output signal;
the quadrature-phase AM RF input signal is a quadrature-phase polar-modulated RF input signal; and
the quadrature-phase AM RF output signal is a quadrature-phase polar-modulated RF output signal.

23. The RF circuitry of claim 1 wherein the WAMPSIS is a digital signal.

24. The RF circuitry of claim 1 wherein the baseband controller comprises a digital-to-analog converter (DAC) adapted to receive and convert the stream of windowed AMIS samples from digital form to analog form to provide the WAMPSIS.

25. A baseband controller comprising:
a baseband processor adapted to:
window a stream of amplitude modulation input signal (AMIS) samples to create a stream of windowed AMIS samples, such that:
the stream of AMIS samples is divided into a stream of input windows and the stream of windowed AMIS samples is created from a stream of output windows;
each output window is created from a corresponding input window; and
each input window includes N of the stream of AMIS samples and each output window provides M of the stream of windowed AMIS samples, such that under at least certain operating conditions, N is greater than one; and
interface circuitry adapted to provide a windowed amplitude modulation power supply input signal (WAMPSIS) using the stream of windowed AMIS samples,
wherein an amplitude modulation (AM) power supply is adapted to provide an AM power supply output signal based on the WAMPSIS, and a power amplifier stage is adapted to:
receive and amplify an AM radio frequency (RF) input signal to provide an AM RF output signal; and
use the AM power supply output signal to provide power for amplification.

26. The baseband controller of claim 25 wherein the interface circuitry comprises a digital-to-analog converter (DAC) adapted to receive and convert the stream of windowed AMIS samples from digital form to analog form to provide an AM power supply input signal.

27. A method comprising:
windowing a stream of amplitude modulation input signal (AMIS) samples to create a stream of windowed AMIS samples, such that:
the stream of AMIS samples is divided into a stream of input windows and the stream of windowed AMIS samples is created from a stream of output windows;
each output window is created from a corresponding input window; and
each input window includes N of the stream of AMIS samples and each output window provides M of the stream of windowed AMIS samples, such that under at least certain operating conditions, N is greater than one; and
providing a windowed amplitude modulation power supply input signal (WAMPSIS) using the stream of windowed AMIS samples;
providing an amplitude modulation (AM) power supply output signal based on the WAMPSIS;
receiving and amplifying an AM radio frequency (RF) input signal to provide an AM RF output signal; and
using the AM power supply output signal to provide power for amplification.

* * * * *